US012620494B2

(12) United States Patent
Naghavi

(10) Patent No.: US 12,620,494 B2
(45) Date of Patent: *May 5, 2026

(54) PREDICTING ADVERSE HEALTH RISK BASED ON CT SCAN IMAGES AND AI-ENABLED CARDIOVASCULAR STRUCTURE VOLUMETRY

(71) Applicant: Morteza Naghavi, Long Beach, CA (US)

(72) Inventor: Morteza Naghavi, Long Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/167,691

(22) Filed: Feb. 10, 2023

(65) Prior Publication Data

US 2024/0120105 A1 Apr. 11, 2024

Related U.S. Application Data

(60) Provisional application No. 63/414,546, filed on Oct. 9, 2022.

(51) Int. Cl.
*G16H 50/30* (2018.01)
*A61B 5/02* (2006.01)
(Continued)

(52) U.S. Cl.
CPC .............. *G16H 50/30* (2018.01); *A61B 5/02* (2013.01); *A61B 6/032* (2013.01); *G16H 30/20* (2018.01)

(58) Field of Classification Search
CPC ........ G16H 50/30; G16H 30/20; G16H 30/40; G16H 50/20; A61B 5/02; A61B 6/032;
(Continued)

(56) References Cited

U.S. PATENT DOCUMENTS

2015/0238270 A1* 8/2015 Raffy ..................... A61B 90/37
600/407
2017/0199189 A1* 7/2017 Wade .............. G01N 33/56955
(Continued)

OTHER PUBLICATIONS

Peter L.M. Kerkhof, Heart Failure Phenotypes Require Sex-Specific Criteria Which Are Based on Ventricular Dimensions, Jul. 2019 (Year: 2019).*

*Primary Examiner* — Hajime Rojas
(74) *Attorney, Agent, or Firm* — Pham Law PLLC; Frank Pham

(57) ABSTRACT

Embodiments of the invention relate generally to systems and methods for facilitating determining a risk of a patient for an adverse health outcome. In one embodiment, an inventive method includes using an AI-enabled volume calculator to estimate cardiac structure volume from CT scan images; and using a computer enabled risk calculator to, based at least in part on the estimated volume, determine a risk of a patient for an adverse health condition. In some embodiments, a system for detecting patients at risk of an adverse health condition includes a computer enabled volume calculator configured to facilitate assessing the volume of a cardiovascular structure based at least in part on a set of CT scan images; the system can include a computer enabled risk calculator configured to determine, based at least in part on the assessed volume, whether the patient is at risk for an adverse health condition.

13 Claims, 20 Drawing Sheets

(51) Int. Cl.
    *A61B 6/03*            (2006.01)
    *G16H 30/20*        (2018.01)

(58) Field of Classification Search
    CPC ....... A61B 6/4417; A61B 6/463; A61B 6/481;
                A61B 6/541; A61B 5/7275; A61B 6/503;
                                     A61B 6/5217
    See application file for complete search history.

(56)                         References Cited

U.S. PATENT DOCUMENTS

| | | | |
|---|---|---|---|
| 2018/0218502 A1* | 8/2018 | Golden | ...................... G06T 7/11 |
| 2021/0334962 A1* | 10/2021 | Min | ..................... A61B 8/5223 |
| 2022/0260589 A1* | 8/2022 | Stubbe | ................... G01N 33/74 |
| 2022/0405915 A1* | 12/2022 | Gordon | ................. G16H 50/20 |

* cited by examiner

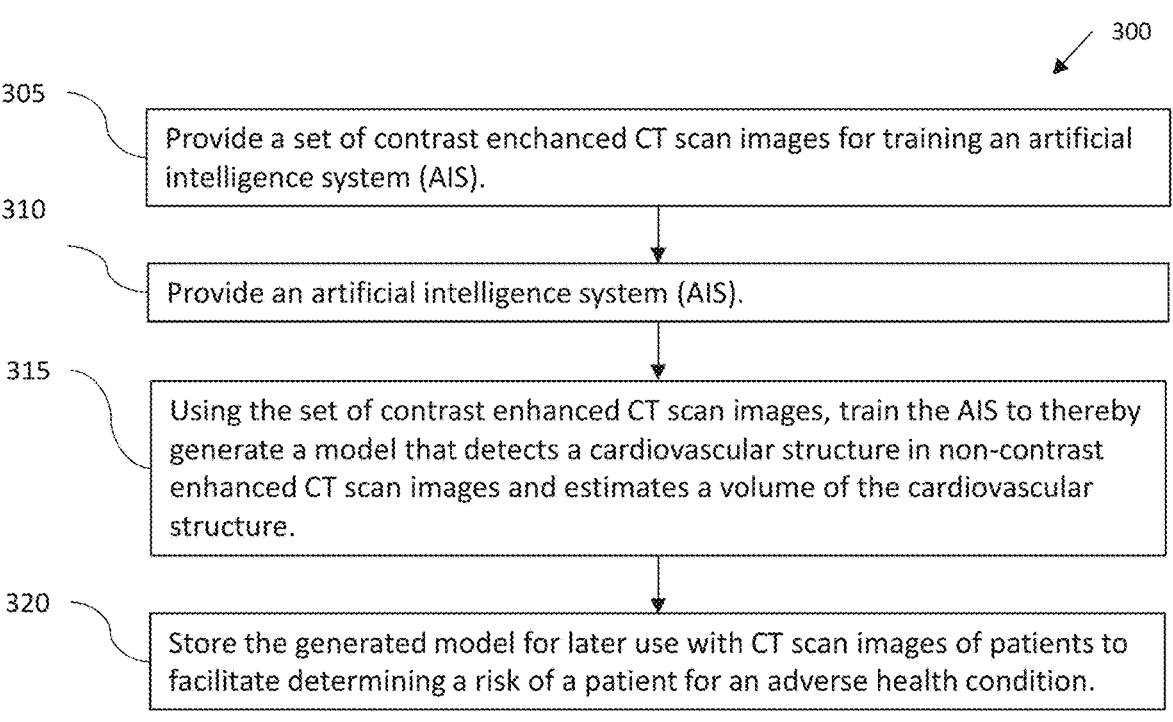

305 — Provide a set of contrast enchanced CT scan images for training an artificial intelligence system (AIS).

310 — Provide an artificial intelligence system (AIS).

315 — Using the set of contrast enhanced CT scan images, train the AIS to thereby generate a model that detects a cardiovascular structure in non-contrast enhanced CT scan images and estimates a volume of the cardiovascular structure.

320 — Store the generated model for later use with CT scan images of patients to facilitate determining a risk of a patient for an adverse health condition.

*FIG. 3*

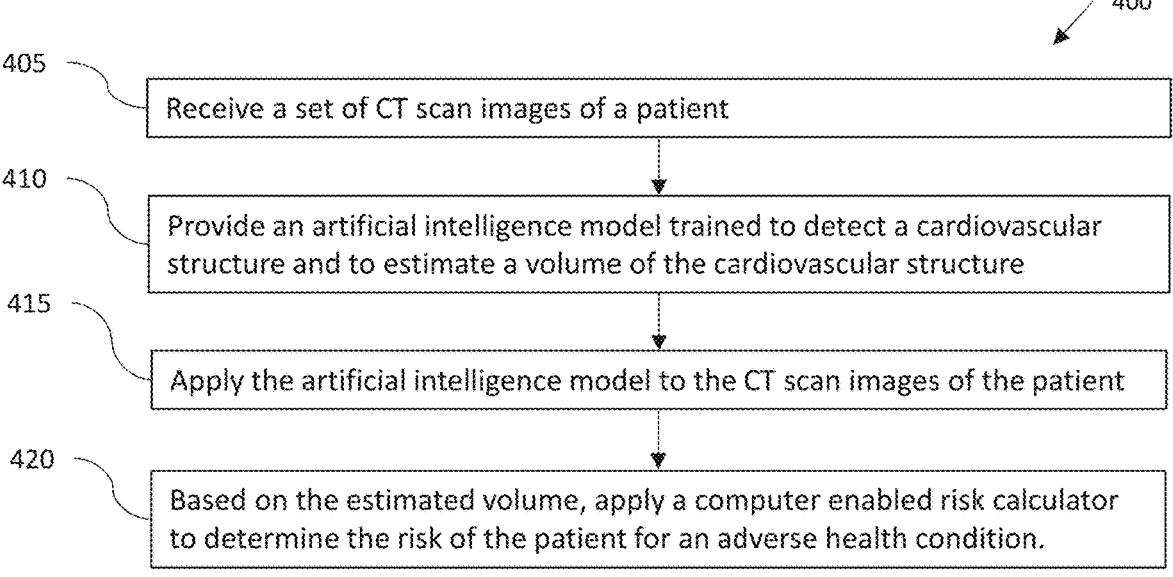

405 — Receive a set of CT scan images of a patient

410 — Provide an artificial intelligence model trained to detect a cardiovascular structure and to estimate a volume of the cardiovascular structure 415 — Apply the artificial intelligence model to the CT scan images of the patient 420 — Based on the estimated volume, apply a computer enabled risk calculator to determine the risk of the patient for an adverse health condition.

PHILLIPS RA

PHILLIPS RV

PHILLIPS LA

PHILLIPS LV

CUMULATIVE INCIDENCE OF HF BY LV VOLUME
TOP QUARTILE
(ADJUSTED BY AGE, GENDER, BSA)

CUMULATIVE INCIDENCE OF HF BY LV VOLUME
QUARTILES
(ADJUSTED BY AGE, GENDER, BSA)

HFrEF vs. HFpEF by LV VOLUME

HFrEF vs. HFpEF by LV VOLUME INDEX

FIG. 28A

PREDICTING ADVERSE HEALTH RISK BASED ON CT SCAN IMAGES AND AI-ENABLED CARDIOVASCULAR STRUCTURE VOLUMETRY

RELATED APPLICATIONS

This application claims priority to U.S. provisional patent application 63/414,546, filed on Oct. 9, 2022, which is hereby incorporated in its entirety herein by reference.

BACKGROUND

Field

Embodiments of the invention relate generally to system and methods for determining the risk of a person for an adverse health condition. In particular, embodiments of the invention are directed to systems and methods for using non-invasive images to train an artificial intelligence model to facilitate estimating the volume of a cardiovascular structure. Based at least in part on the estimated volume, a risk of an adverse health condition can be determined.

DESCRIPTION OF RELATED ART

For coronary artery disease certain screening and diagnostic tools are known, such as coronary artery calcium (CAC) score and coronary CT angiography. And for predicting atrial fibrillation (AF) and heart failure (HF) it is known to use, for example, CHARGE-AF and brain natriutic peptide (BNP). CHARGE AF is an epidemiological risk calculator. BNP is more precise than CHARGE-AF but it is not specific to left atrial and ventricular function.

AF is the most common sustained arrhythmia and is associated with an increased risk of stroke and cardiovascular mortality. In the United States, at least 3 to 6 million people have AF. It is predicted that the number of AF patients will increase to over 12 million cases by 2030, imposing a significant economic burden with projected healthcare expenses of $260 million. In Europe, prevalent AF in 2010 is about 9 million among individuals older than 55 years and is expected to reach 14 million by 2040. It is estimated that by 2050 at least in 72 million individuals in Asia will be diagnosed with AF, and about 3 million with AF-related strokes. This presents a public health crisis especially for the growing elderly population in coming decades.

Medicare services costs are significantly higher among AF patients than non-AF patients; therefore early treatment is critical to limit the disease burden imposed by AF. The adverse social and public health effects of HF are even worse. It is estimated that by 2030, more than 8 million Americans will have HF. And the total direct medical costs of HF are expected to rise from $21 billion to $53 billion.

The 5-year survival rates of AF are of concern. Without proper treatment, 51% of AF patients will die within five years. Although the economic burden posed by AF and HF are critical in light of the increasing healthcare costs, early detection tools and preventive interventions for pre-AF and pre-HF patients are currently unavailable. One report shows that 96,860 strokes occurred within 1 year among patients with AF, with an associated total direct lifetime cost of nearly $8 billion. Of these costs, $2.6 billion in direct costs are incurred during the first year after the stroke.

HF poses an even greater threat to US healthcare system. Given the rising rates of hospitalization and rehospitalization, HF is associated with a significant cost burden. Approximately 1% to 2% of the total US health care budget is spent on HF, and half of that is attributable to late diagnosis leading to inpatient admissions for HF. This challenge presents a great opportunity to make an impact on the healthcare system by early detection and interventions of subclinical HF and AF. Currently, BNP and CHARGE-AF are the only available tools for early detection of high-risk patients for AF and HF. A combination of high-risk CHARGE-AF and a 7-day ECG patch has been reported. CHARGE-AF is an epidemiological risk calculator that can be useful as a population based measure, but it is not preferred as applied to individual patients as needed in a physician's office. A more direct assessment is preferred such as by imaging the cardiac chambers where AF happens.

It is known to calculate a CHARGE-AF score: $0.508 \times age$ (5 year increments)$+0.248 \times height$ (10 cm increments)$+0.115 \times weight$ (15 Kg increments)$+0.197 \times systolic$ blood pressure (20 mm Hg increments)$-0.101 \times diastolic$ blood pressure (10 mm Hg increments)$+0.359 \times current$ smoker$+0.349 \times antihypertensive$ medication$+0.237 \times diabetes+0.701 \times congestive$ heart failure$+0.496 \times myocardial$ infarction. See, "Simple risk model predicts incidence of atrial fibrillation in a racially and geographically diverse population: the CHARGE-AF consortium." J Am Heart Assoc. 2013 Mar. 18; 2 (2): e000102. doi: 10.1161/JAHA.112.000102. PMID: 23537808; PMCID: PMC3647274.

It is known to use manual measurements of left ventricle chamber in a single-slice to predict HF. However, rapid and accurate acquisition of whole heart volume parameters is challenging. Even though semi-automated delineation and quantification of cardiovascular structures can be useful in CT images, currently known methods still require a significant degree of manual modifications, which is time-consuming and may increase inter-/intra-observer variability.

Over a billion will die from cardiovascular disease, most being unaware of their risk die prematurely. The need for early detection of pre-symptomatic cardiovascular disease is unmet. So is the need for inexpensive, reliable and scalable technology. CAD can be assessed by a CAC scan. Blood pressure and lipid levels are easily measured, but currently, other cardiac anatomical risk factors cannot be quantified without complex testing.

Currently, no screening tool is available for detecting individuals at high risk of AF and/or HF. Despite the critical need no biomarker is currently available to identify individuals at high risk for AF or HF and their complications. An ideal biomarker would help to detect individuals at high risk for both AF and HF. Embodiments of the systems and methods disclosed here address these and other needs in the relevant art.

SUMMARY OF ILLUSTRATIVE EMBODIMENTS

Data integration projects face challenges bringing together the right expertise. There are pipeline behaviors that can be common across multiple pipelines. However, under known methods, typically pipeline behaviors are not developed once and made reusable by different pipelines. Some embodiments disclosed herein address the need for scale where dozens of projects may be concurrently active.

In one embodiment, the invention is addressed to an artificial intelligence (AI) enabled method of detecting patients at risk of an adverse health condition. In one embodiment, the method involves receiving CT scan images and storing them in a computer file; using an AI-enabled enabled volume calculator, estimating a volume of a cardiovascular structure based on the CT scan images stored in said computer file; and using a computer enabled risk calculator, and based at least in part on the estimated volume, determining the risk of the patient for an adverse health condition. In some embodiments, obtaining CT scans includes obtaining non-contrast enhanced CT scans.

In certain embodiments, obtaining CT scan images includes obtaining one or more of the group comprising: ECG-gated cardiac CT scans, non-gated cardiac CT scans, non-gated full chest CT scans, low dose lung cancer screening CT scans, and a combination of contrast enhanced and non-contrast enhanced chest CT scans.

In one embodiment, the cardiovascular structure is a one or more of the group comprising left atrium (LA), left ventricle (LV), left ventricular wall (LVW), right atrium (RA), right ventricle (RV), aorta, and pulmonary artery. In some embodiments, estimating the volume further involves adjusting one more of variables from the group consisting of: patient's age, gender, height, weight, body surface area, body mass index, and ethnicity. In certain embodiments, determining the risk of the patient for an adverse health condition comprises determining one or more conditions from the group consisting of: atrial fibrillation (AF), heart failure (HF), stroke, cerebrovascular events, chronic obstructive pulmonary diseases (COPD), emphysema, dementia, ischemic heart disease, aortic aneurysm, pulmonary hypertension, cardiovascular mortality, and all-cause mortality.

In one embodiment, using a computer enabled volume calculator includes using an artificial intelligence (AI) based model trained with contrast enhanced CT scan images. In some embodiments, using a computer enabled volume calculator involves using an artificial intelligence (AI) based model that converts contrast enhanced CT scan images into non-contrast enhanced CT scan images and vice versa. In certain embodiments, the AI agent is based on one or more of the following: deep learning, machine learning, and rule-based assessment.

In one embodiment, the method can include outputting to a computer enabled display a digital representation of the cardiovascular structure and a graphic presentation of the patient's risk of an adverse health condition. In some embodiments, the computer enabled display is on a mobile application or a web application that can be used by patients or their care providers. In yet other embodiments, the computer enabled display is on a desktop application run on premise to avoid patient data security concerns. In some embodiments, the method can include communicating the CT scan images to cloud storage, subsequently processing the CT scan images with the volume calculator, and subsequently sending the images or the reports to a medical facility.

In certain embodiments, the method can include combining the estimated cardiac structure volume with one or more health related variables to enhance the prediction model, resulting in a multivariate composite index of health to better determine the risk of future adverse health conditions. In some embodiments, the one or more health related variables is one or more of the group comprising: blood pressure, heart rate, blood oxygenation, blood tests, medications, and other patient medical data.

In one aspect, the invention concerns a system for detecting patients at risk of an adverse health condition. In one embodiment the system includes a set of CT scan images stored in a computer file; a computer enabled volume calculator configured to facilitate assessing the volume of a cardiovascular structure based, at least in part, on the set of CT scan images stored in said computer file; and a computer enabled risk calculator configured to determine, based at least on the assessing of the volume of the cardiovascular structure, whether the patient is at risk for an adverse health condition.

In some embodiments, the CT scan images include non-contrast enhanced CT scans. In certain embodiments, the CT scan images include one or more of: ECG-gated cardiac CT scan images, non-gated full chest lung CT scan images, contrast enhanced CT scan images, and non-contrast CT scan images. In one embodiment, the CT scans include at least one chest CT scan.

In some embodiments, the CVD includes one or more of: atrial fibrillation (AF), heart failure (HF), stroke, and cardiac mortality. In certain embodiments, the cardiac structure is one or more of the group consisting of: left atrium (LA), left ventricle (LV), right atrium (RA), right ventricle (RV), left ventricular mass (LVM), thoracic aorta, and pulmonary trunk.

In one embodiment, the volume calculator can include an artificial intelligence (AI) configured to facilitate assessing the cardiovascular structure volume. The AI agent can be based on one or more of: deep learning, machine learning, and rule-based assessment.

In some embodiments, the system can include means for outputting to a computer enabled display the determination of whether the patient is at risk for an adverse health condition. In certain embodiments, the system can include means for communicating to cloud storage in a network, and then subsequently sending to a medical facility, the determination of whether the patient is at risk for an adverse health condition. In one embodiment, the computer enabled display is on a mobile computing device application. In some embodiments, the computer enabled display is on a desktop application.

In another aspect, the invention is directed to an AI-enabled computer program product for facilitating determining a risk of a patient for an adverse health condition. In one embodiment, the computer program product includes one or more computer readable storage media, and program instructions collectively stored on the one or more computer readable storage media. In some embodiments, the program instructions include program instructions to train an artificial intelligence (AI) algorithm utilizing a set of labeled CT scan images data to associate a set of characteristics of the data with a segmentation of cardiovascular structures and volume estimate of cardiovascular structures in the labeled CT scan images; program instructions to receive a new set of unlabeled CT scan images data; program instruction to apply the AI algorithm to the new unlabeled CT scan images data to segment cardiovascular structures and to estimate a volume of each of the cardiovascular structures; and program instructions to provide a graphical representation including the segmented cardiovascular structures and the estimated volumes.

In some embodiments, the computer program product can include program instructions for determining a risk of patient for an adverse health condition based at least in part on the estimated volume of a cardiovascular structure. In certain embodiments, the set of labeled CT scan images includes contrast enhanced CT scan images. In one embodiment, the set of unlabeled CT scan images includes non-contrast enhanced CT scan images.

In yet another aspect, the invention concerns a system for detecting patients at risk of developing atrial fibrillation. In one embodiment, the system includes a set of non-invasive cardiac images stored in a computer file; a computer enabled volume calculator configured to estimate the volume of a left atrium, based at least in part on the set of non-invasive cardiac images; and a computer enabled risk calculator configured to determine, based at least on the assessing of the volume of the left atrium, an estimate of a risk of developing atrial fibrillation (AF). In some embodiments, the system can include a computer enabled health adviser configured, based at least on a patient's age, gender, ethnicity, body surface size, and other health related conditions, to recommend a wearable cardiac monitoring device for monitoring episodes of atrial fibrillation and/or for alerting patients to take preventive actions against a future cerebrovascular event.

In some embodiments, the non-invasive cardiac images are obtained from one or more of the group comprising: computed tomographic scans, echocardiographic scans, and magnetic resonance imaging scans. In certain embodiments, the wearable cardiac monitoring device is one of: wearable ECG devices, ECG patches, ECG embedded blood pressure cuffs, photoplethysmography (PPG) devices, and wearables devices capable of detecting atrial fibrillation and alerting the patient.

In one embodiment, the risk calculator can be further configured to determine, based at least in part on a systemic marker of health, the estimate of risk of developing AF. The systemic marker of health can be, for example, a serum brain natriuretic protein or a non-invasive physiologic marker. In some embodiments, the non-invasive marker of health is, for example, electrocardiography data and/or photoplethysmography data.

Another aspect of the invention is directed to a system for detecting patients at risk of developing heart failure with reduced ejection fraction (HFrEF) versus heart failure with preserved ejection fraction (HFpEF). In one embodiment, the system includes a set of non-invasive cardiac images stored in a computer file; a computer enabled volume calculator configured to, based at least on the set of non-invasive cardiac images, estimate a cardiac structure volume; and a computer enabled risk calculator configured to determine, based at least on the assessing of the cardiac structure volume, a risk of developing HFrEF versus HFpEF.

In one embodiment, the set of non-invasive cardiac images comprises images obtained from one or more of: computed tomographic scan images, echocardiographic scan images, or magnetic resonance imaging scan images.

In some embodiments, the computer enabled risk calculator is configured to, based at least on the assessing of a left ventricle volume, distinguish HFrEF from HFpEF in patients with heart failure symptoms. In certain embodiments, the cardiac structure is at least one of: left atrium (LA), left ventricle (LV), right atrium (RA), and right ventricle (RV).

In one embodiment, the risk calculator can be further configured to determine, based at least in part on a systemic marker of health, the estimate of risk of developing HFrEF versus HFpEF. The systemic marker of health can be, for example, a serum brain natriuretic protein or a non-invasive physiologic marker. In some embodiments, the non-invasive marker of health is, for example, electrocardiography data and/or photoplethysmography data.

In one embodiment, the system can include a computer enabled health adviser configured to, based at least on patient's age, gender, ethnicity, body surface area, cardiometabolic risk factors, past medical history, and other health related conditions, facilitate recommending a treatment plan to take preventive actions against a future cardiovascular event.

Additional features and advantages of the embodiments disclosed herein will be set forth in the detailed description that follows, and in part will be clear to those skilled in the art from that description or recognized by practicing the embodiments described herein, including the detailed description which follows, the claims, as well as the appended drawings.

Both the foregoing general description and the following detailed description present embodiments intended to provide an overview or framework for understanding the nature and character of the embodiments disclosed herein. The accompanying drawings are included to provide further understanding and are incorporated into and constitute a part of this specification. The drawings illustrate various embodiments of the disclosure, and together with the description explain the principles and operations thereof.

BRIEF DESCRIPTION OF THE DRAWINGS

A more complete understanding of the embodiments, and the attendant advantages and features thereof, will be more readily understood by references to the following detailed description when considered in conjunction with the accompanying drawings wherein:

FIG. 3 is a flowchart of a method of generating an artificial intelligence model for facilitating determining a risk of a patient for an adverse health condition according to embodiments of the invention disclosed here.

FIG. 4 is a flowchart of a method of applying an artificial intelligence model for facilitating determining a risk of patient for an adverse health condition according to embodiments of the invention disclosed here.

7

Figure 11:
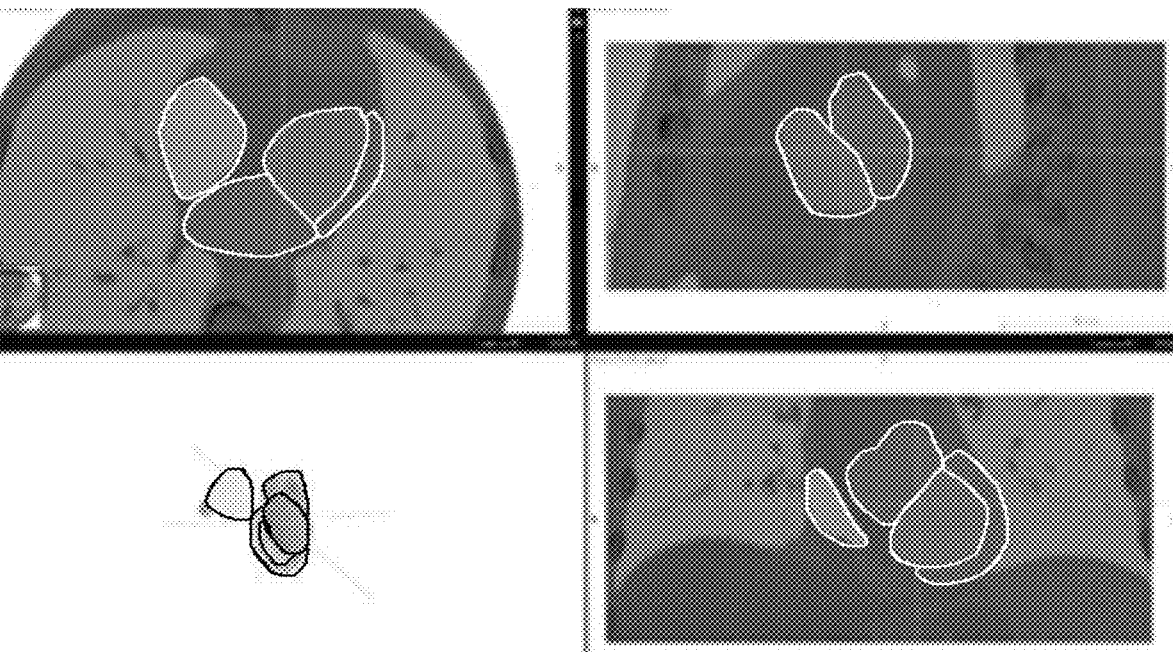

FIG. 11 shows imaging and segmentation in ECG-gated cardiac scan or volume measurements as performed by certain embodiments of the systems and methods disclosed herein.

Figure 12:
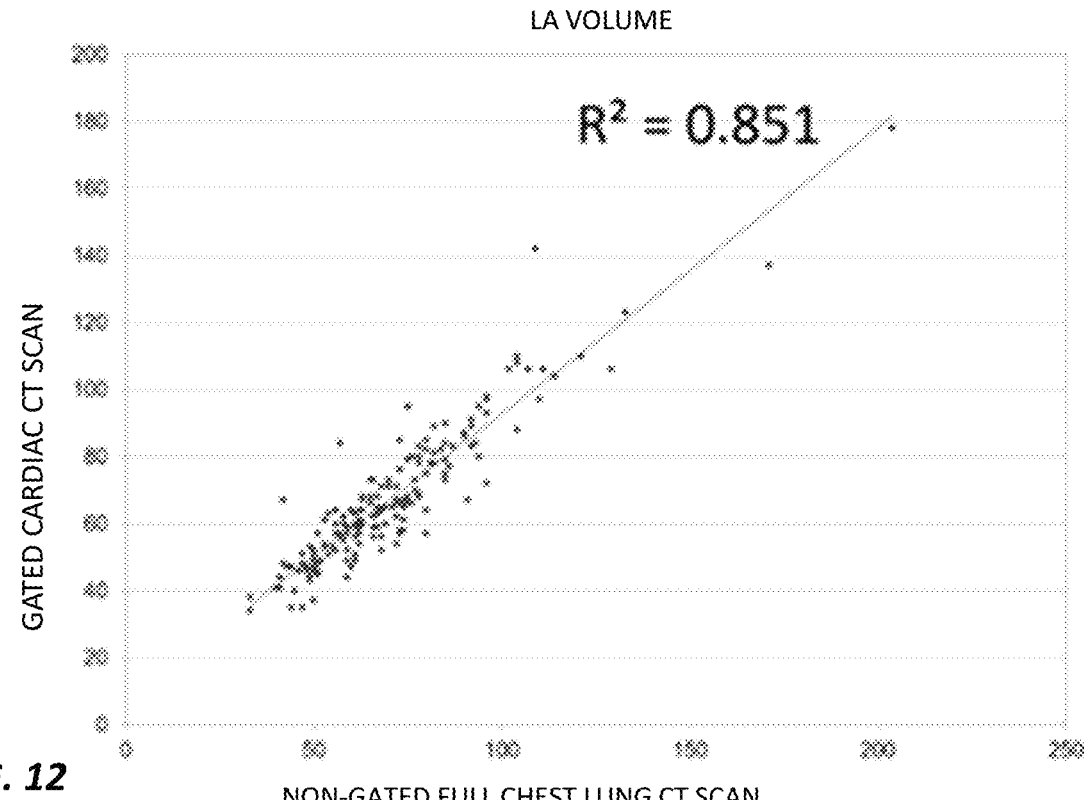

FIG. 12 shows a correlation associated with LA volumetry performed by embodiments of the invention versus conventional methods.

Figure 13:
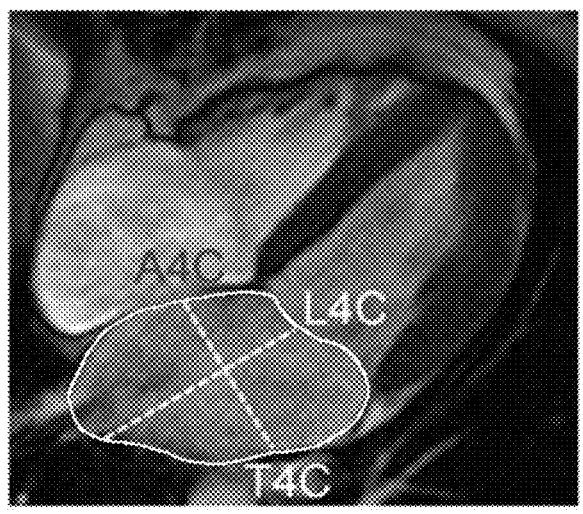

FIG. 13 is an image illustrating LV volumetry performed by conventional methods.

Figure 14:
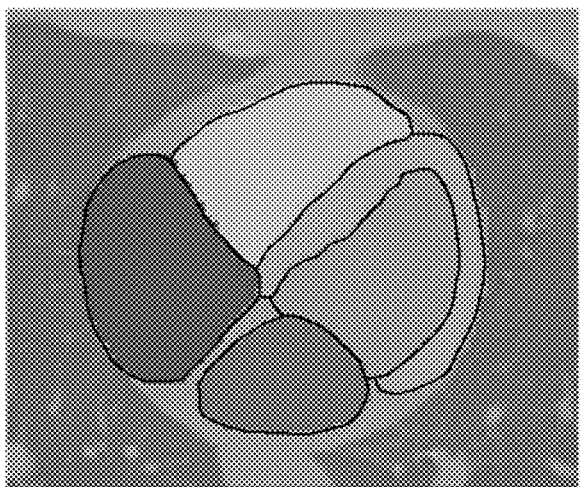

FIG. 14 is an image illustrating segmentations for LA, LV, RA, RV volumetry as performed by certain embodiments of the systems and methods disclosed herein.

Figure 15:
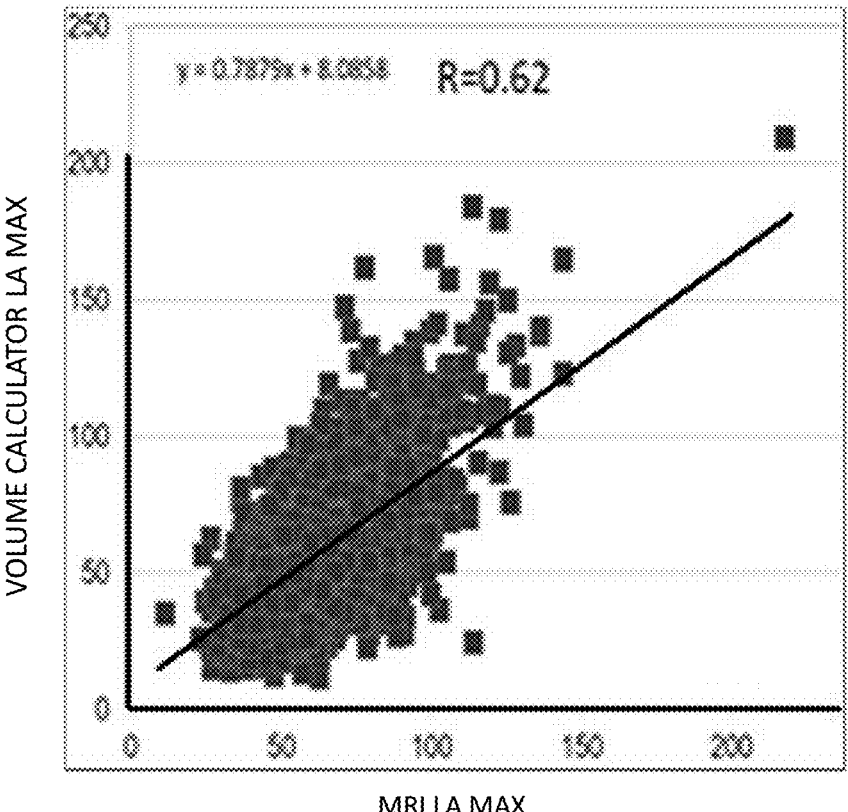

FIG. 15 is a graph showing a correlation associated with the LA volumetry performed by embodiments of the invention versus conventional methods using contrast enhanced cardiac MRI for maximum LA volume.

Figure 16:
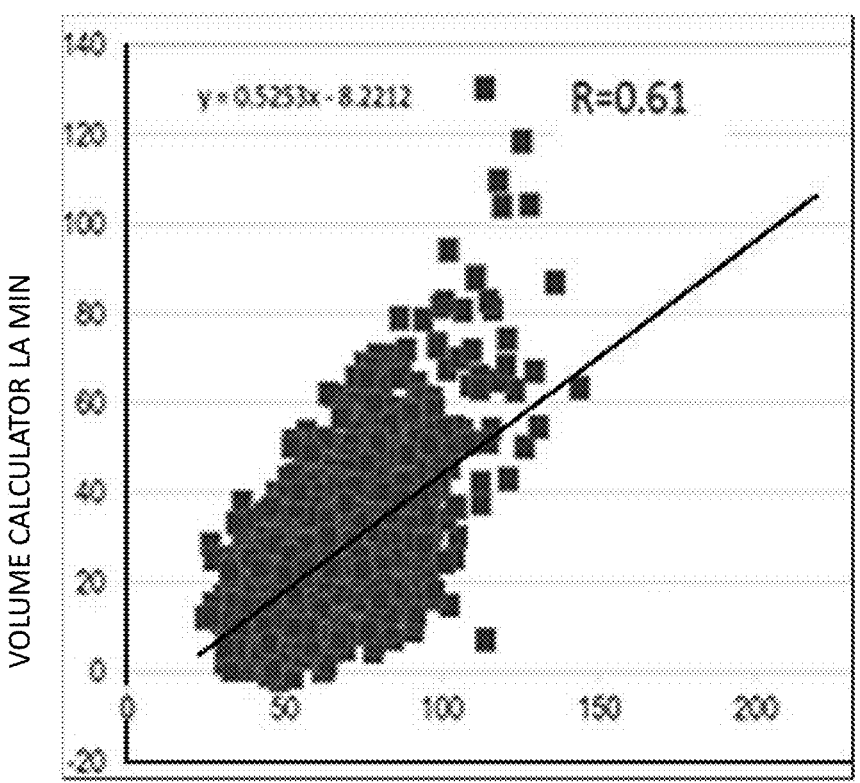

FIG. 16 is a graph showing another correlation associated with the LA volumetry performed by embodiments of the invention versus conventional methods using contrast enhanced cardiac MRI for minimum LA volume.

Figure 17:
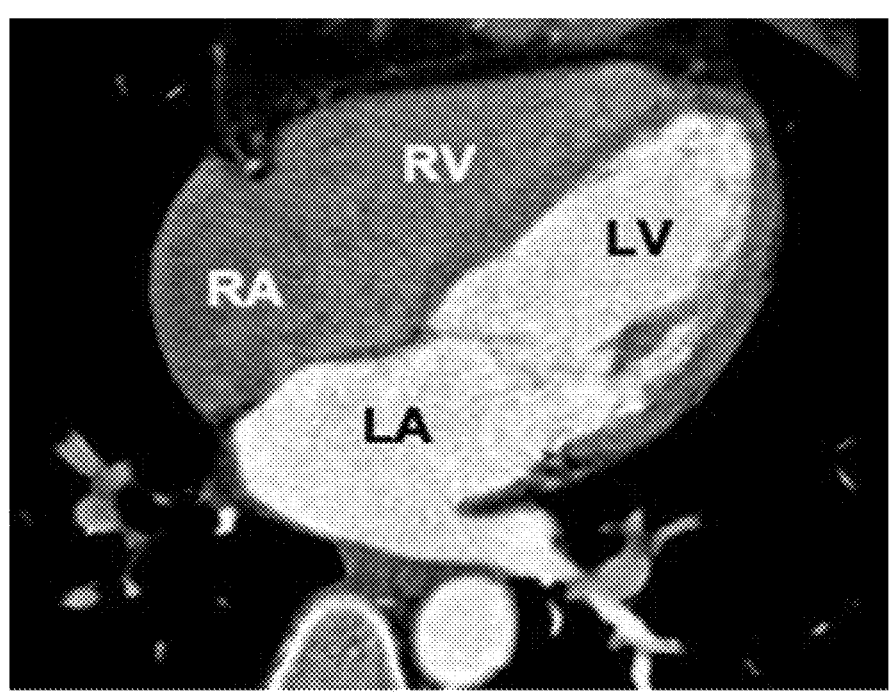

FIG. 17 is an image illustrating an example of imaging for LA, LV, RA, and RV measurements performed by conventional methods.

Figure 18:
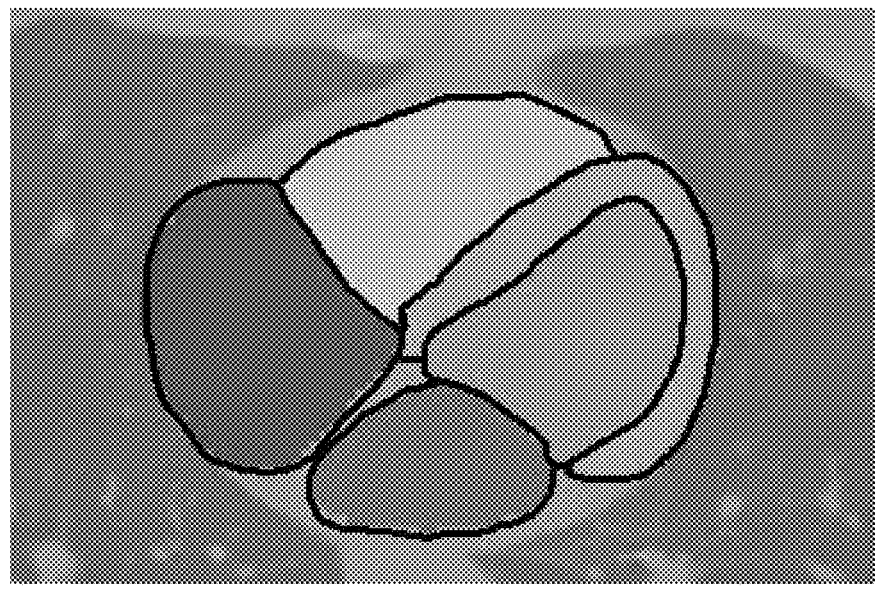

FIG. 18 is an image illustrating an example of imaging for LA, LV, RA, and RV measurements performed by certain embodiments of the systems and methods disclosed herein.

Figure 19:
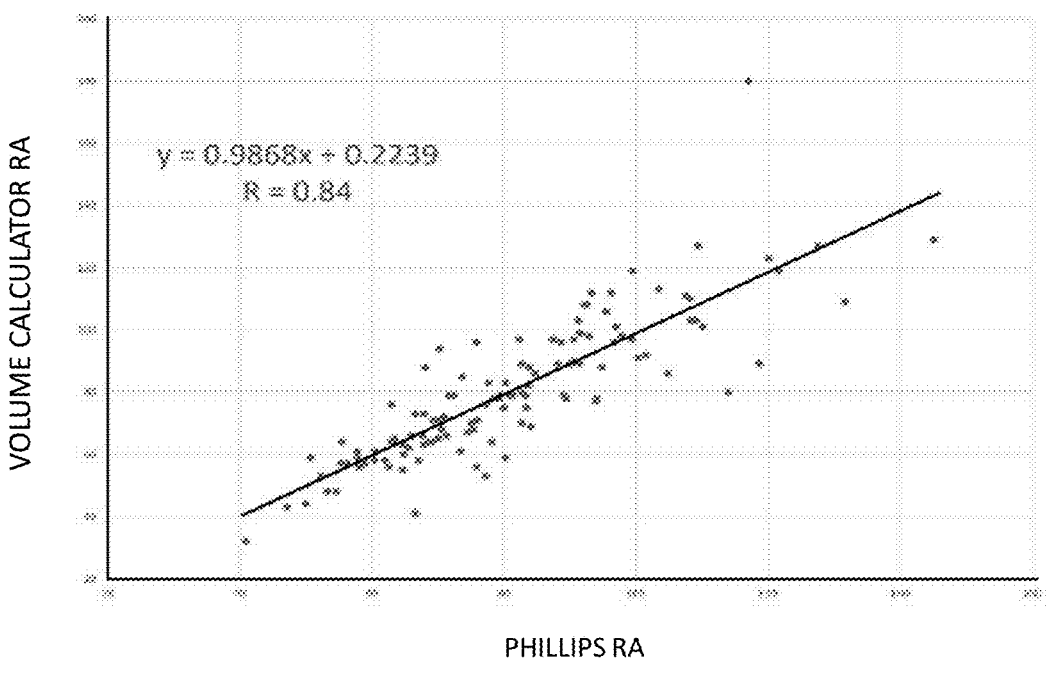

FIG. 19 is a graph showing a correlation associated with the RA volumetry performed by embodiments of the invention versus conventional methods.

Figure 20:
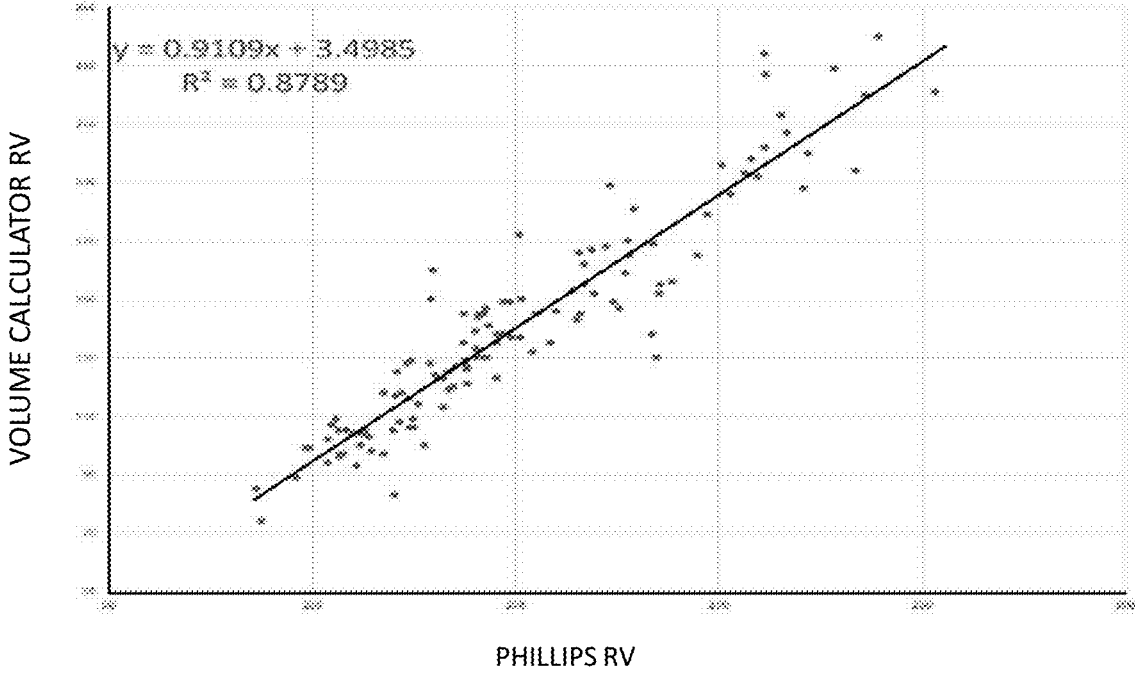

FIG. 20 is a graph showing a correlation associated with the RV volumetry performed by embodiments of the invention versus conventional methods.

Figure 21:
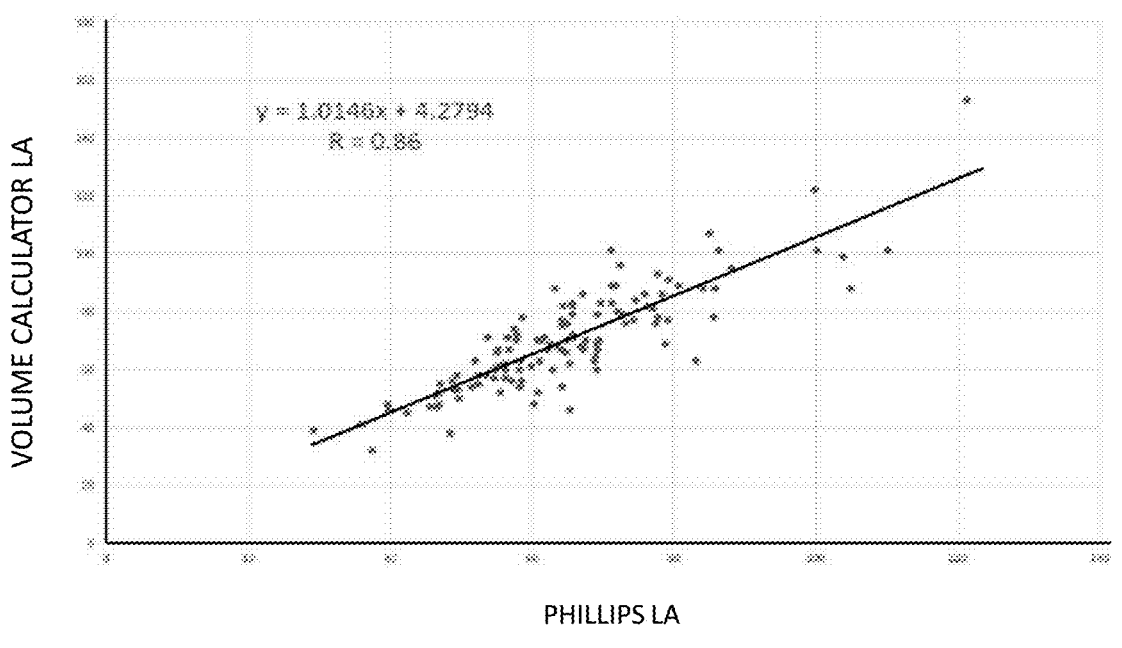

FIG. 21 is a graph showing a correlation associated with the LA volumetry performed by embodiments of the invention versus conventional methods.

Figure 22:
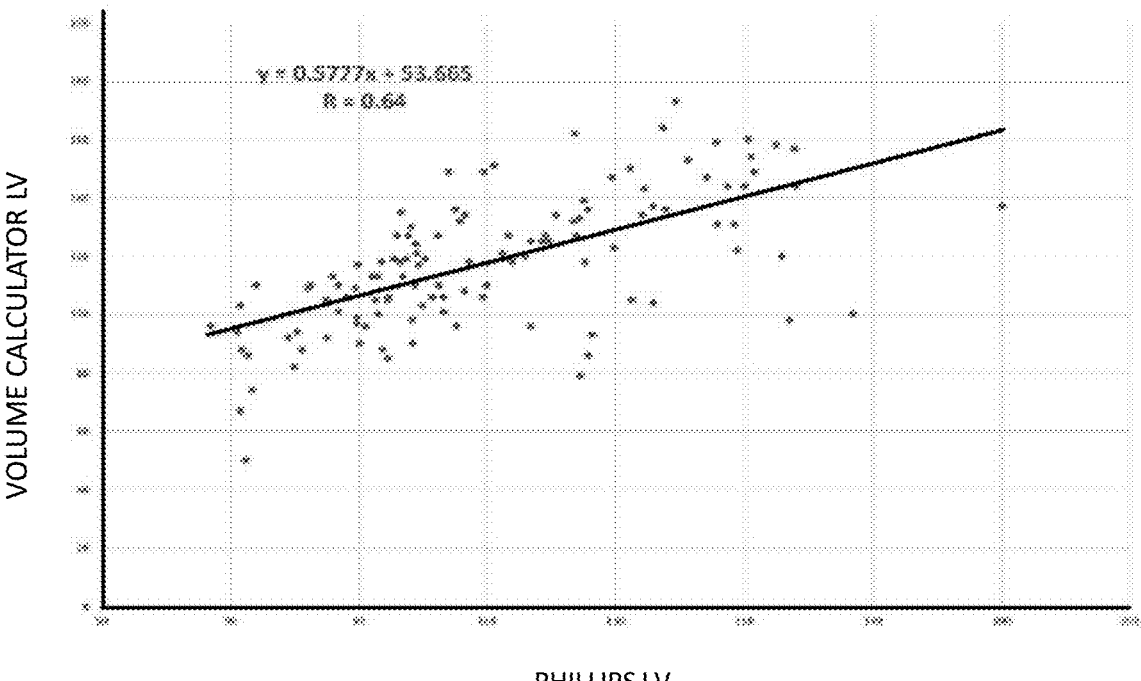

FIG. 22 is a graph showing a correlation associated with the LV volumetry performed by embodiments of the invention versus conventional methods.

Figure 23:
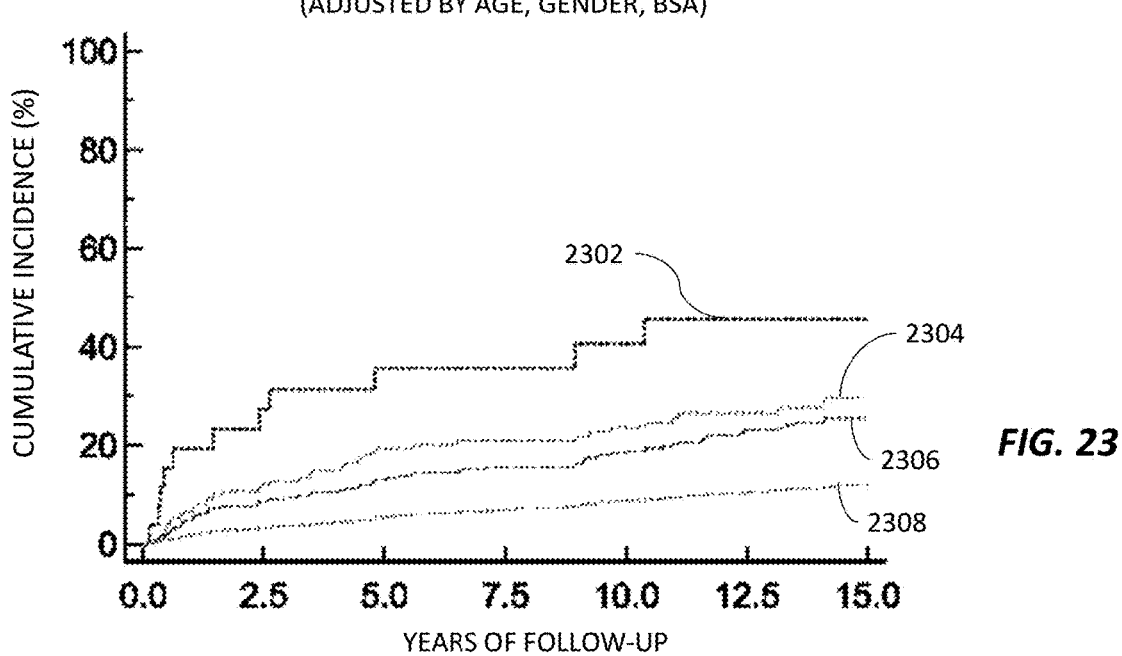

FIG. 23 is a graph showing cumulative incidence of HF by LV volume as performed by certain embodiments of the systems and methods disclosed herein.

Figure 24:
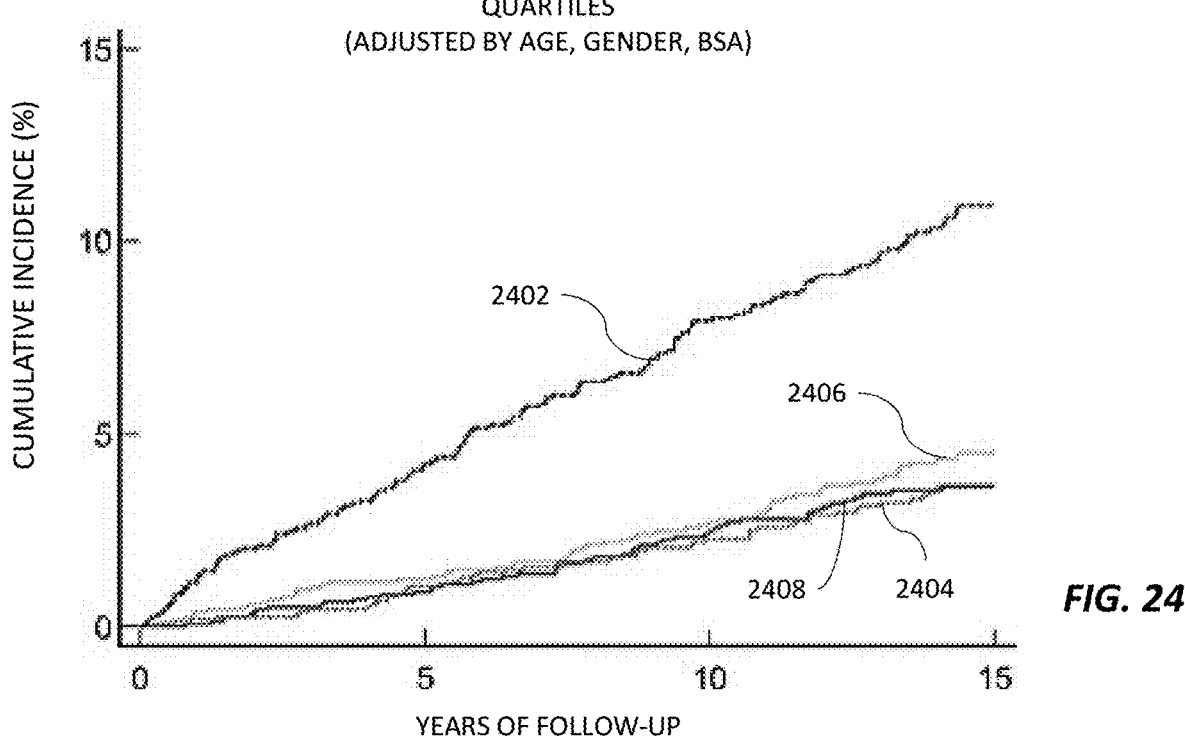

FIG. 24 is a graph showing cumulative incidence of HF by LV volume quartiles as performed by certain embodiments of the systems and methods disclosed herein.

Figure 25:
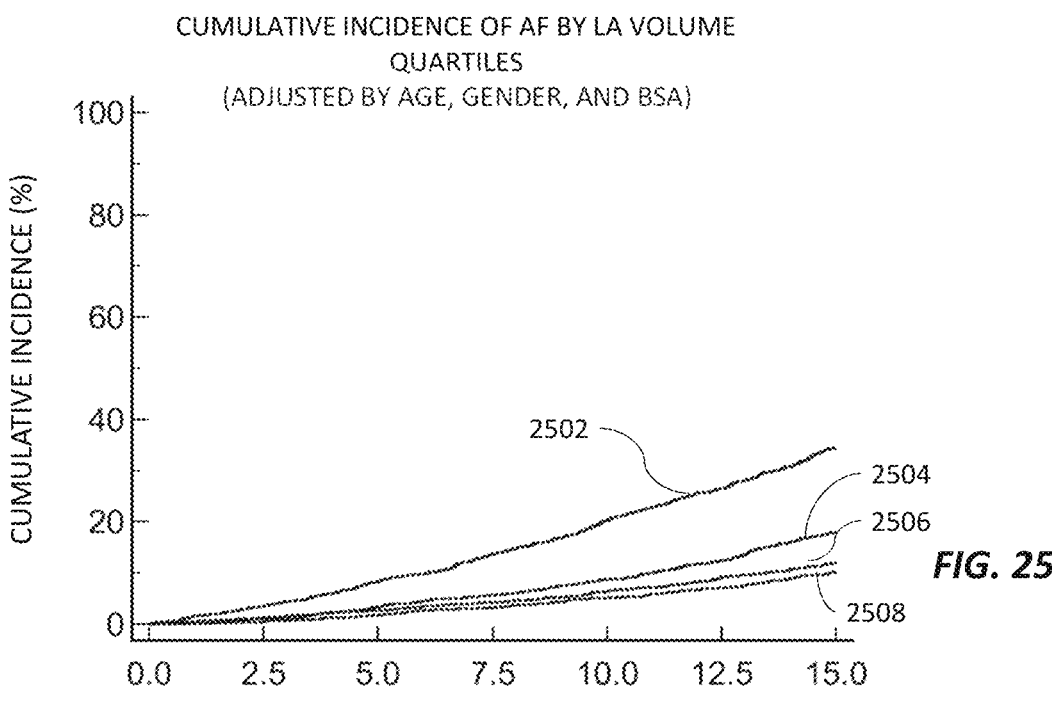

FIG. 25 is a graph showing cumulative incidence of AF by LA volume as performed by certain embodiments of the systems and methods disclosed herein.

Figure 26:
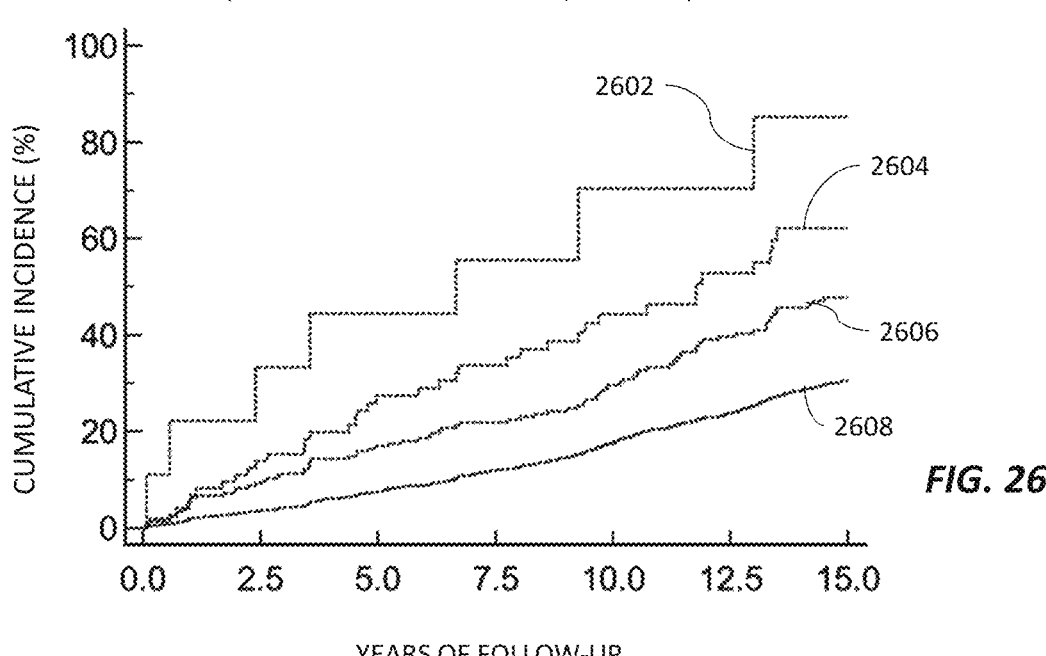

FIG. 26 is a graph showing cumulative incidence of AF by LA volume as performed by certain embodiments of the systems and methods disclosed herein.

Figure 27:
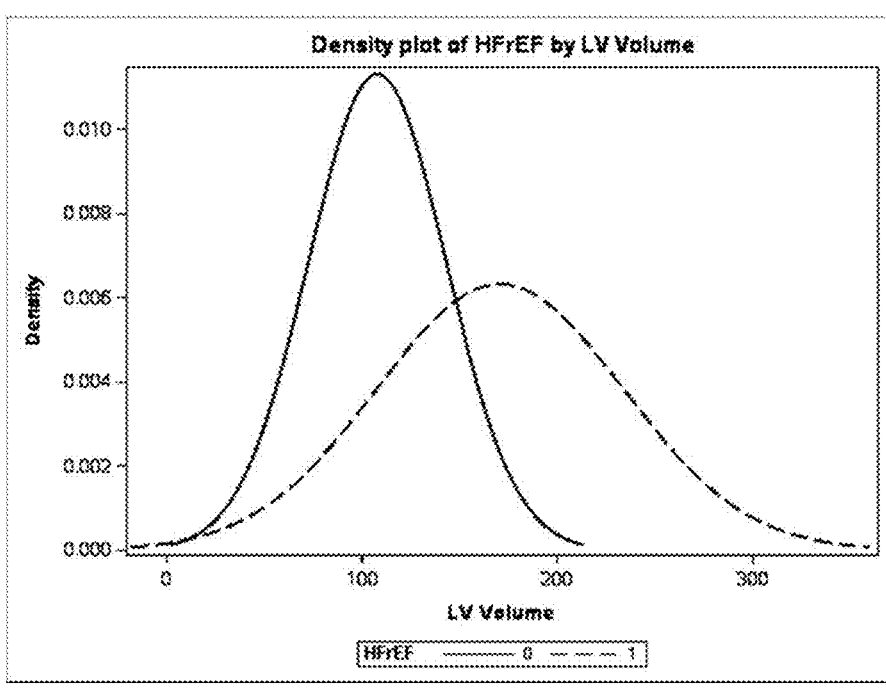

FIG. 27 is a graph showing HErEF versus HEpEF by LV volume as performed by certain embodiments of the systems and methods disclosed herein.

Figure 28:
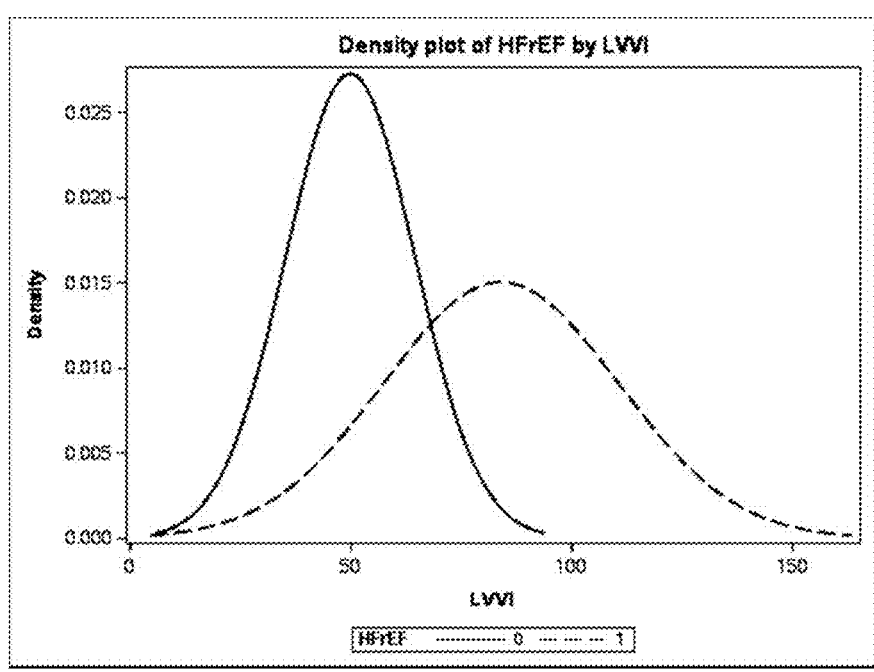

FIG. 28 is a graph showing HErEF versus HEpEF by LV volume index as performed by certain embodiments of the systems and methods disclosed herein.

Figure 28A:
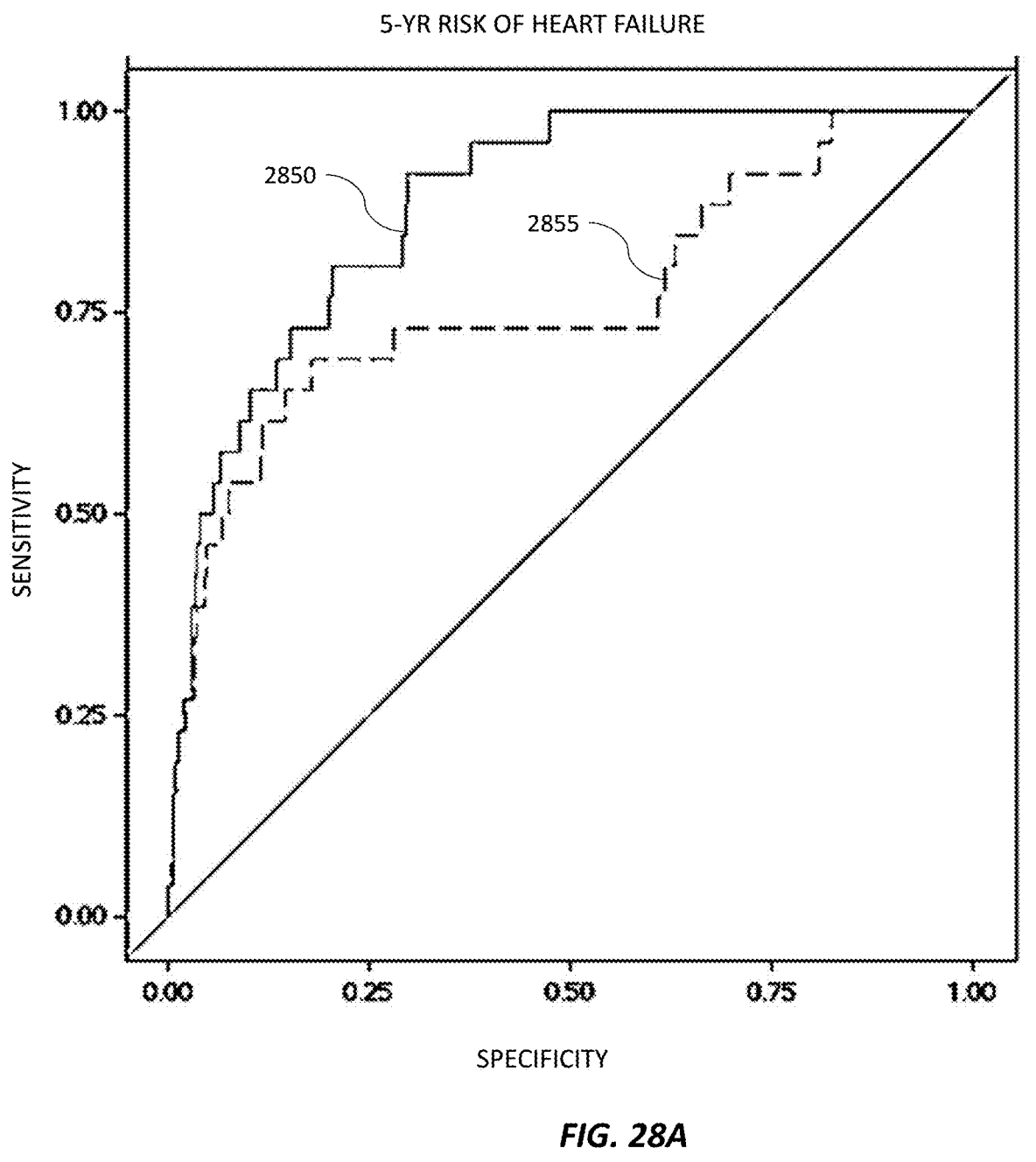

FIG. 28A is a graph showing a prediction model performance, as performed by the inventive methods and system disclosed herein, against a prediction model performed by conventional methods.

Figure 29:
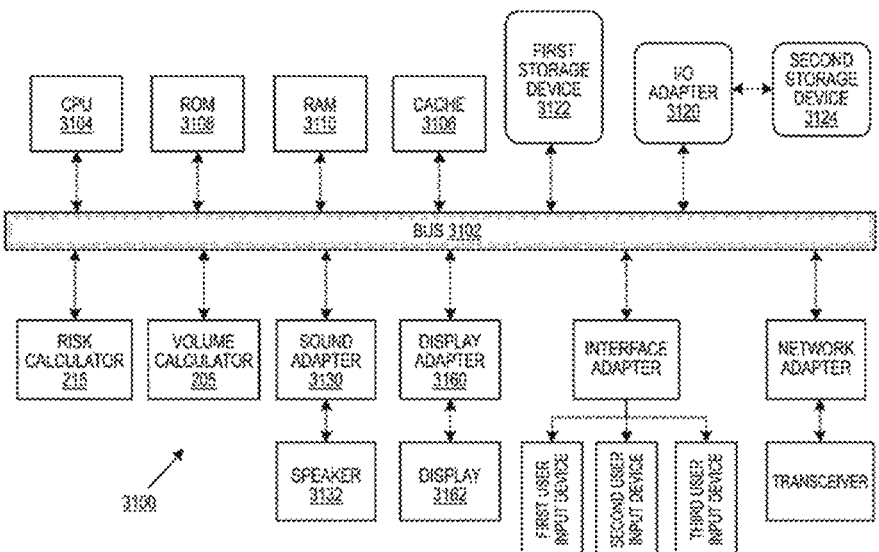

FIG. 29 is a block diagram of a processing system, according to certain embodiments of the systems disclosed herein.

Figure 30:
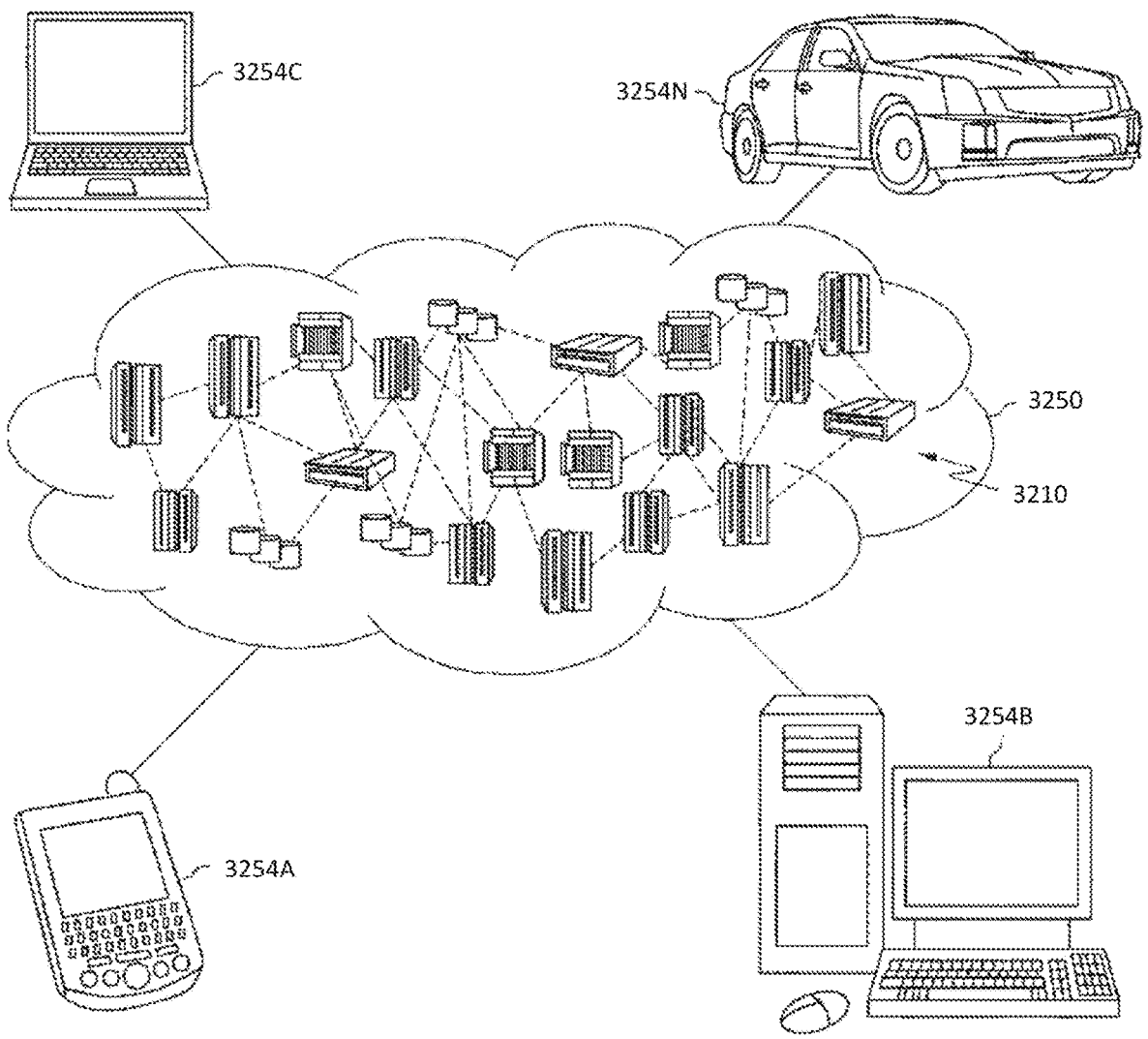

FIG. 30 is a block diagram of an illustrative cloud computing environment having one or more computing nodes with which local computing devices used by cloud customers to communicate, according to embodiments disclosed herein.

Figure 31:
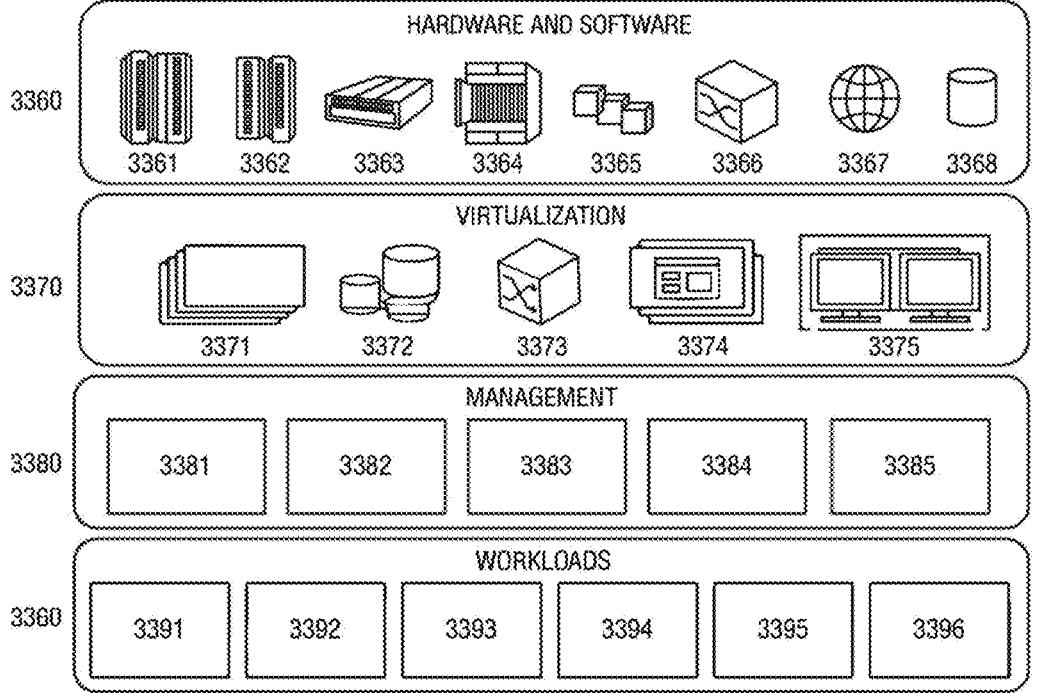

FIG. 31 is a block diagram of a set of functional abstraction layers provided by a cloud computing environment, according to embodiments disclosed herein.

DETAILED DESCRIPTION OF ILLUSTRATIVE EMBODIMENTS

The specific details of the single embodiment or variety of embodiments described herein are set forth in this application. Any specific details of the embodiments are used for demonstration purposes only, and no unnecessary limitation or inferences are to be understood therefrom.

Before describing in detail exemplary embodiments, it is noted that the embodiments reside primarily in combinations of components related to the system. Accordingly, the device components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

In general, the embodiments described herein relate to systems and methods for using AI-enabled automated volumetry of cardiovascular structures. In some embodiments, a system according to the invention is directed to an AI-enabled software module for automated measurement of cardiac chamber volume and left ventricular wall mass that works on non-contrast CT scans, which can be cardiac scans and/or full chest scans. In one embodiment, non-contrast, gated and non-gated, chest CT scans can be used. In some embodiments, the system can identify patients at high risk for developing an adverse health condition, such as AF and heart failure, based on cardiac chamber volume. Embodiments of the systems and methods can facilitate identifying asymptomatic patients at risk of developing atrial fibrillation (AF) and heart failure (HF) based on enlarged left atrium (LA), for example. In one embodiment, the inventive systems and methods can facilitate estimating the volumes of left atrium (LA), left ventricle (LV), right atrium (RA), right ventricle (RV), and left ventricle wall (LVW).

Known systems and methods for measuring the volume of cardiac chambers use contrast-enhanced CT scans, which require more radiation, longer scan times, carry a risk of contrast-induced nephrotoxicity, and demand a higher level of professional staff during the scan. Measurements facilitated by the methods and systems disclosed herein are well correlated with cardiac chambers volumetry measurement using contrast-enhanced CT scans as well as contrast-enhanced cardiac magnetic resonance imaging (CMRI). Measurements, obtained by the inventive methods disclosed, in cardiac CT scans are well correlated with measurements, obtained by the inventive methods disclosed, in full-chest CT scans.

Known methods cannot facilitate detection of asymptomatic individuals at high risk of developing AF or HF based on non-contrast CT scans. The inventive methods and systems disclosed herein can detect asymptomatic individuals at high risk of developing AF or HF based, at least in part, on enlarged left atrium and other cardiac chambers.

Embodiments of the system can provide advantages over existing systems and methods including the potential to reduce or eliminate the need for hospitalization, improve patient quality of life, facilitate patients' ability to manage their own care (such as through self-directed personal assistance), or establish long term clinical efficiencies.

CHARGE-AF is the most widely referenced epidemiological tool for prediction of AF. Similarly, BNP (brain natriuretic peptide) is the most widely used epidemiological tool for prediction of HF. Embodiments of the inventive systems and methods disclosed herein can outperform CHARGE-AF and BNP for prediction of AF and HF respectively. Adding the volumetry estimates, obtained through the inventive systems and methods disclosed here using cardiac CT scans (such as coronary artery calcium (CAC) scan, or lung cancer screening CT scans), makes it very attractive for population health implementation and primary prevention strategies of the leading cause of death and disability in the United States, cardiovascular disease.

Embodiments of the system include an AI-enabled, automated measurement of cardiac chambers that works on CAC scans and identifies individuals at high risk of AF and HF based on enlarged left atrium and other cardiac chambers.

Over 80 million CT scans are performed in the United States each year. Among them, 95% are non-electrocardiogram (ECG)-gated, low-dose chest screening CT scans for lung cancer screening. Currently, no screening tool is available for identifying patients at high risk of AF or/and HF. CAC scoring represents only a small fraction of all the information available in non-contrast cardiac CT scans.

A digital health screening tool that works on both on ECG-gated cardiac scans and non-gated full lung scans is desirable because it can be used with any coronary artery calcium and lung cancer screening CT scans and provide benefits without additional costs.

Currently, manual segmentation and delineation of one heart with attached great arteries by a well-trained radiologist or cardiologist takes about 30 minutes. However, in some embodiments of the invention disclosed here, a convolutional neural network (CNN) and a vision transformer model (such as U-Net/vision transformer) system can outperform human experts in cardiac segmentation. This segmentation takes less than about 5 seconds in some embodiments.

In certain embodiments, the system detects discrepancies between the myocardium and blood pool that are imperceptible to the human eye. This is a sea change to current interpretation and analysis of cardiovascular structures in a routine CAC or lung cancer screening. Currently, such an analysis is not practiced in clinical.

The AI-enabled approach can add significant values to currently known cardiovascular and lung cancer preventive care, and can reduce healthcare resource disparities by making such an effective, intelligent auxiliary diagnostic tool available through a Software-as-a-Service (SaaS) implementation. In some embodiments, cloud infrastructure and APIs can facilitate implementation of the system as a medical SaaS product to hospitals and imaging centers. Embodiments of the system can be implemented on cloud-based web and mobile app platforms.

In one embodiment, the system can be validated against, for example, a pool of cardiac MRI cases. In some embodiments, the system can be validated against coronary CT angiography cases (for example, 131 never before seen cases). In certain embodiments, the system can be validated against ECG-gated cardiac and non-gated lung scans. Embodiments of the system can use CAC scans and/or lung cancer screening scans, providing benefits without additional imaging cost and/or radiation.

Embodiments of the system can quantify the volume of each cardiac chamber including left atrium (LA), left ventricle (LV), right atrium (RA), right ventricle (RV), LV wall mass, aorta and pulmonary artery from non-contrast CT scans.

Cardiac chamber sizes and left ventricular mass measured by embodiments of the system disclosed here can facilitate predicting future AF, stroke, and HF. Embodiments of the system can use, for example, chest CT scans (either CAC or lung cancer screening scans).

In some embodiments, the system can include a deep learning model to facilitate obtaining accurate measurements of the volume of cardiac chambers and the left ventricular mass from standard, non-contrast chest CT scan images. In some embodiments, the process takes about 5-15 seconds (FIG. 5A-7).

Figure 9:
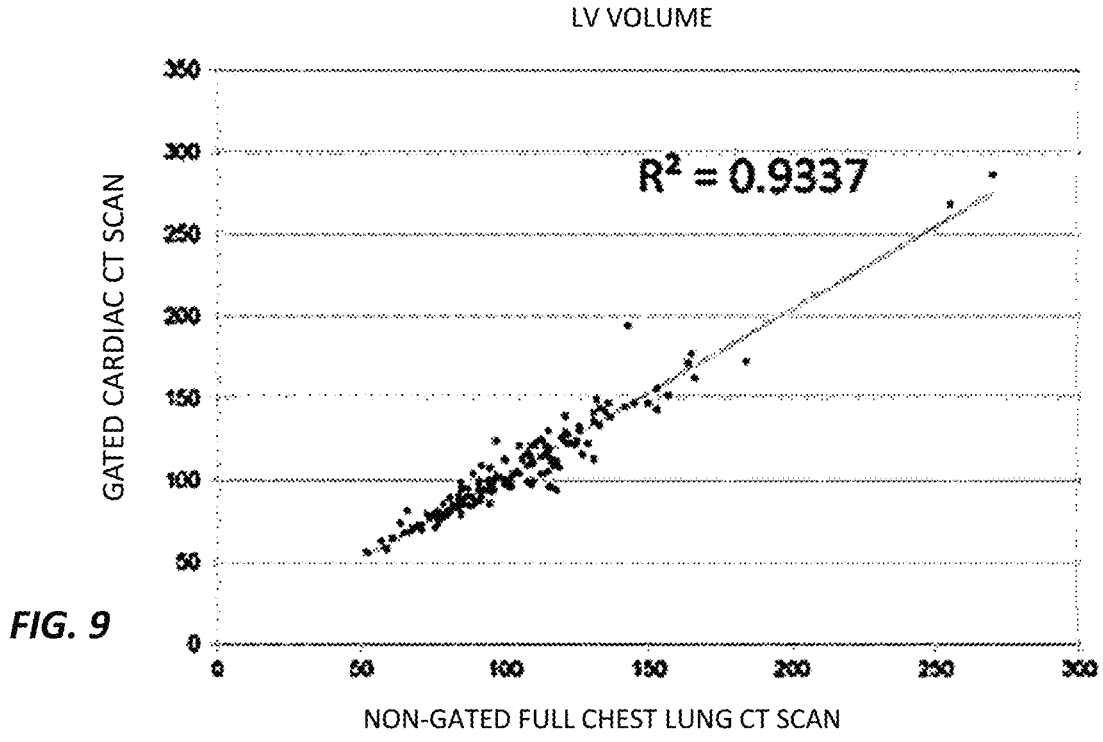
FIG. 9 is a graph illustrating a correlation associated with LV volume estimates performed by embodiments of the invention versus conventional methods.

The system shows good correlations with MRI/CTA and AF/HF outcomes data. The results obtained with some embodiments of the system show that gated and non-gated CT chest scan based are strongly correlated (FIG. 9, FIG. 12). Also, the results are comparable to both cardiac MRI (FIG. 15, FIG. 16) and contrast enhanced cardiac CT angiography scans (FIG. 19-22).

Currently, cardiac CT scans are used to image coronary arteries and echocardiography/MRI is used for heart size and hypertrophy evaluation. Embodiments of the system can use one low-cost, reliable technique to assess both aspects of cardiac pathology without subjecting a patient to additional radiation and contrast agents, which in some patients cause nephrotoxicity.

Embodiments of the methods and system disclosed here can substantially shift the role of the calcium score scan, a technique that has remained unchanged (in terms of data and analysis) for about thirty years. Adding volumetric information to the calcium score data can cause the combined volumetry/LVH/calcium score measurements be the most accurate imaging predictor of cardiovascular events available, and possibly the standard of care for preventive cardiology including subclinical coronary artery disease, HF, and detecting pre-AF cases for stroke prevention.

Cardiovascular risk stratification has largely stalled post CAC. While improved calibration and application of CVD risk calculators has occurred, multiple attempts to improve risk prediction with biomarkers or contrast imaging (i.e., CTCA) have not shown benefit with acceptable cost-effectiveness.

Accurate assessment of cardiac chamber sizes, LV mass, aortic size and calcifications, can improve cardiac risk prediction over standard risk equations. A substantial shift in accuracy can move clinical practice from purely Framingham-inspired (cholesterol, BP, smoking) to a combined imaging and risk factor/biomarker approach, changing the paradigm of clinical risk assessment.

Embodiments of the system can impact the conducting of clinical trials for prevention of symptomatic HF and AF. For example, by selecting the top 1 or 5 percentiles of LA size measured by the system disclosed here in a large scale clinical trial, pharmaceutical initiatives can effectively conduct therapeutic intervention trials with a reasonable and affordable sample size.

Results can be visually inspected, and volumetry compared corresponding MRI data. Characteristics of the CT scans resulting in poor volume estimates can be examined. The fine-tuning adjustment of the volumetry algorithms can be performed with selection of the best algorithm and rules to maximize correlation and validation.

In one embodiment, contrast enhanced cardiac CT scans and non-contrast cardiac CT scans can be obtained as part of coronary CT angiography to transfer segmentations of cardiovascular structures from contrast enhanced images to non-contrast images. In some embodiments, the images can be taken from the same patient within minutes and both are ECG gated; hence, the images can be fully registered and the contrast enhanced areas of each cardiovascular structure can be overlapped with the corresponding area in the non-contrast images of the same patient. Since this image is from the same examination, the image is well aligned with the contrast enhanced image.

In one embodiment, if a minor misalignment is detected a human expert can correct the segmentations in the non-contrast images before training. In some embodiments, after a transfer of segmentations, a UNET deep learning system can be used for training an artificial intelligence (AI) model. In certain embodiments, iterative training can be implemented based on human supervised correction of mistakes made by the AI model and inputting the corrected segmentations into the AI model for enhanced training.

Referencing FIG. 9 and FIG. 12, embodiments of the systems and methods disclosed herein show good correlations between volumetry measurements of cardiovascular structures by the AI model on non-contrast CT scan cases vs contrast enhanced CT scans of the same cases. These cases were not used for either training, calibration or testing of the AI model.

Referencing FIG. 19-22, embodiments of the systems and methods disclosed herein performed volume measurements of the left atrium in a pool of known cases. The correlations versus the cardiac MRI of the same cases are very good.

In some embodiments, manual editing of segmentation may be required as part of supervised learning. Similarly the system can be improved by patching the model with rules to handle issues related to image acquisition. In some embodiments, a calibration factor can be used to reduce noise effects and CT based LV mass measurements versus MRI. Outputs can be inspected and case failures, and pursue iterative enhancement.

Cardiac chamber volumes are typically measured clinically with ultrasound (echocardiography) or MRI, which are generally considered as the reference standard for clinical care but on a population health level they fall short. As screening tools, echocardiography can be highly operator dependent, and MRI can be excessively high cost and time consuming. More importantly, they cannot detect CAC and are not suitable for lung cancer screening, neither is cardiac CT angiography (ECG gated CT with contrast injection).

Embodiments of the system correlate with MRI for the measurement of LA size, LV end diastolic size, RV end diastolic size and LV mass. Embodiments of the system can delineate the left ventricular wall, outer myocardium, and right ventricle.

One potential limitation of standard CT and calcium score methods is that mid diastole, rather than end diastole is measured. For example, mid diastolic volumes can be converted to end-diastolic measurements with certain ML interpolation, with excellent accuracy. Various machine learning and deep learning and image processing tools can be used to maximize the performance of the system.

The system was used in analyses of AF and HF cumulative incidences with LA and LV volumes based top percentiles. The results show a strong predictive value for LA and LV sizes for prediction of high-risk pre-AF and pre-HF patients who are unaware of their future risk.

Risk factors including LV hypertrophy, which is independent of coronary calcification and can standalone, can be more powerful predictors of HF events than CAC. However, cardiac MRI for this purpose is prohibitively expensive.

Echocardiography is also more expensive than the system and requires 1:1 allocation of sonographers. Conversely, a non-contrast CT scan is inexpensive, non-invasive, can be performed in less than 5 minutes, and is highly automated. The system can improve cardiovascular risk assessment and provide a CVD screening triad for CAD, HF, and AF.

Figure 1:
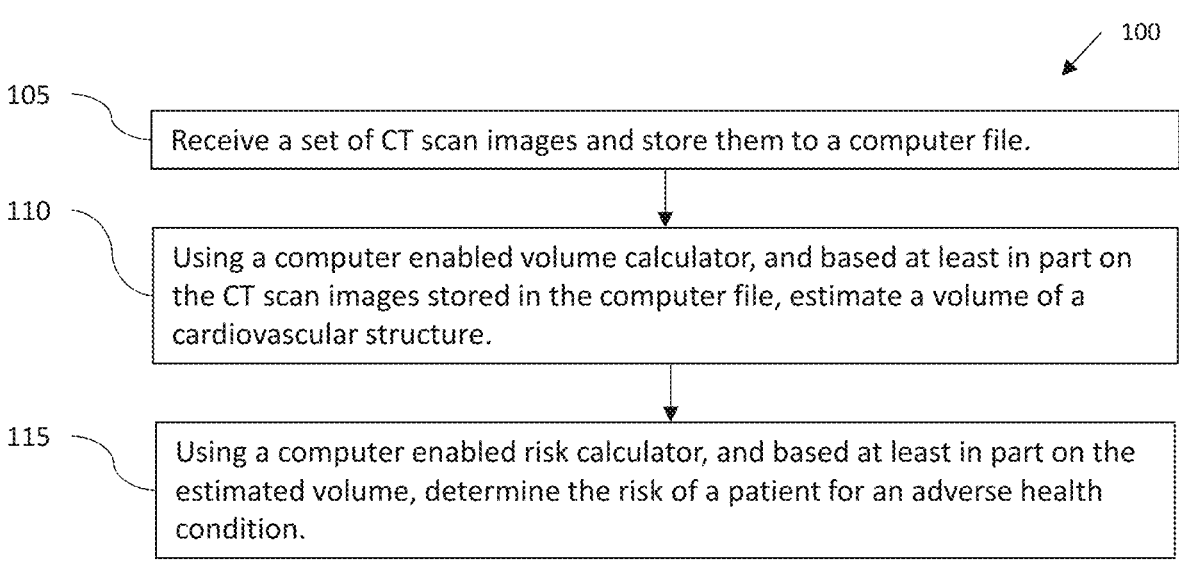
FIG. 1 is a flowchart of a method of determining a risk of a patient for an adverse health condition according to embodiments of the invention disclosed herein.

Referencing FIG. 1, method 100 of determining a risk of a patient for an adverse health condition according to one embodiment of the invention is described. At step 105, a set of CT scan images is received and stored in a computer file. In some embodiments, image processing can be applied to the CT scan images to facilitate improving the accuracy of estimating a volume of a cardiovascular structure. At step 110, a computer enabled calculator can be used to estimate a volume of a cardiovascular structure. A suitable computer enabled calculator can be an artificial intelligence (AI) model trained to segment cardiovascular structures and to estimate cardiovascular structure volumes. The AI model can include a deep learning model, machine learning model, and/or rule-based assessment. In some embodiments, the AI model can be trained with contrast enhanced CT scan images. In certain embodiments, the AI model can convert contrast enhanced CT scan images into non-contrast enhanced CT scan images and vice versa. At step 115, a computer enabled risk calculator can be used with the estimated volume to determine a risk of a patient for an adverse health condition. In one embodiment, a computer enabled risk calculator can be a multivariate risk analyzer based, at least in part, on heart failure incidence risk and ROC AUC data. Correlations between cardiac structure volume estimates and heart failure outcome can be used to configure a suitable risk calculator, which can be a multivariate risk calculator.

Figure 2:
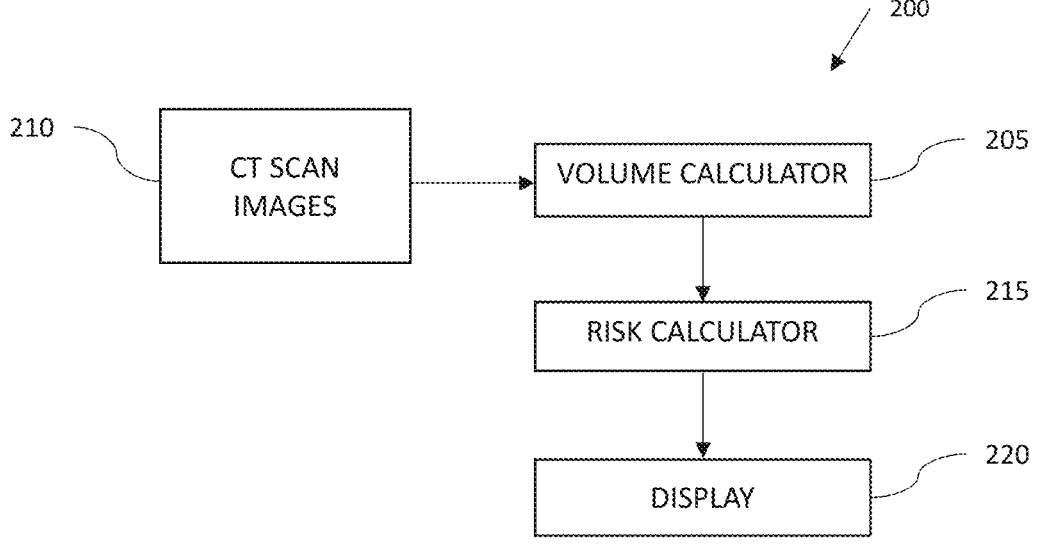
FIG. 2 is a block diagram of a system for determining a risk of patient for an adverse health condition according to embodiments of the invention disclosed here.

FIG. 2 illustrates system 200 for facilitating determining a risk of patient for an adverse health condition according to one embodiment of the invention disclosed here. System 200 can include volume calculator 205. In some embodiments volume calculator 205 includes an AI model configured to facilitate determining a volume of a cardiovascular structure. In certain embodiments, system 200 can include CT scan images 210, which can be stored in a computer memory, for example. CT scan images can include images obtained from CT scans, for example, contrast enhanced CT scans, non-contrast enhanced CT scans, ECG-gated cardiac CT scans, non-gated cardiac CT scans, non-gated full chest CT scans, low dose lung cancer screening CT scans, and a combination of contrast enhanced and non-contrast enhanced chest CT scans. In some embodiments the cardiovascular structure can be, for example, left atrium (LA), left ventricle (LV), left ventricular wall (LVW), right atrium (RA), right ventricle (RV), aorta, and/or pulmonary artery.

System 200 can, in one embodiment, include risk calculator 215 configured to take as input the estimated volume of the cardiovascular structure and to determine, based at least in part on the estimated volume, a risk of a patient for an adverse health condition. In certain embodiments, the adverse health condition can be, for example, atrial fibrillation (AF), heart failure (HF), stroke, cerebrovascular events, chronic obstructive pulmonary diseases (COPD), emphysema, ischemic heart disease, cardiovascular mortality, and all-cause mortality. In some embodiments, the risk is determined based on the estimated volume and taking into account other variables, such as patient's age, gender, height, weight, body surface area, body mass index, and ethnicity, for example. In some embodiments, the estimated volume can be used with one or more health related variables to enhance the prediction model, resulting in a multivariate composite index of health to better determine the risk of future adverse health conditions. In certain embodiments, the one or more health related variables can be, for example, blood pressure, heart rate, blood oxygenation, blood tests, medications, and other patient medical data.

In certain embodiments, system 200 can include display 220 configured for displaying the cardiovascular structure, the estimated volume, and/or a graphic representation of the risk determined by risk calculator 215. In one embodiment, computer enabled display 220 can be on a mobile application or a web application that can be used by patients and/or care providers. In some embodiments, computer enabled display 220 can be on a desktop application run on premises to, for example, avoid patient data security concerns.

FIG. 3 illustrates method 300 of generating an artificial intelligence model for facilitating determining a risk of patient for an adverse health condition according to embodiments of the invention disclosed here. At step 305, a set of CT scan images can be provided for training an artificial intelligence system (AIS). Preferably, the CT scan images are processed, through suitable images processing algorithms, to optimize the training. At step 310 an AIS can be provided. The AIS can be, for example, a computer enabled and implemented convolutional neural network (CNN). One such CNN can be, for example, U-Net. At step 315, using supervised learning, for example, the AIS can be trained to detect/segment cardiovascular structures from the set of CT scan images. In some embodiments, using supervised learning (for example), the AIS can be further trained to estimate a volume of a cardiovascular structure. As a result of the training a model is generated that can be applied to CT scan images of specific patients at a later time. At step 320, the model generated by the training is stored for later use to facilitate determining a risk of a specific patient for an adverse health condition.

FIG. 4 illustrates method 400 of applying an artificial intelligence model for facilitating determining a risk of a patient for an adverse health condition according to embodiments of the invention disclosed here. At step 405, a set of CT scan images of a specific patient can be received. At step 410, an AIS model trained to detect cardiovascular structures and to estimate a volume of a cardiovascular structure can be provided. At step 415, the AIS can be applied to the set of CT scan images to determine the volume of at least one cardiovascular structure. At step 420, based at least in part on the estimated volume, a computer enabled risk calculator can be applied to determine the risk of the patient for an adverse health condition.

Figure 5A:
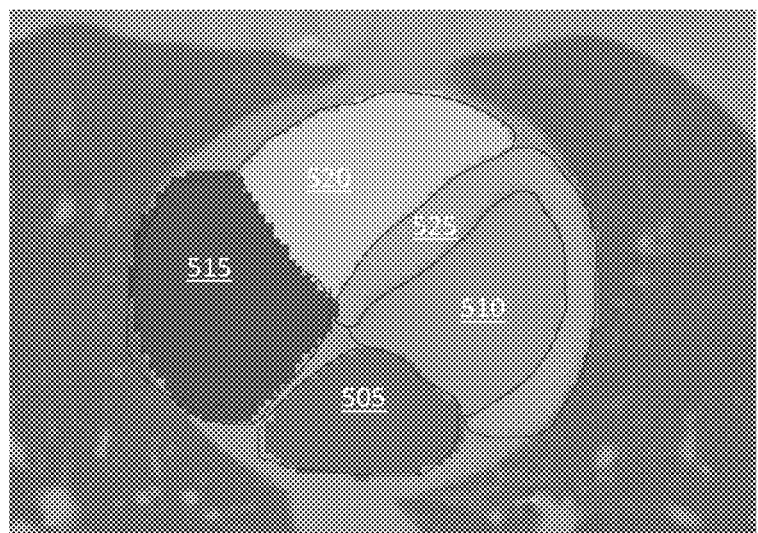
FIG. 5A-5C are images illustrating examples of segmentations for cardiovascular structure volume measurements performed by, and according to, embodiments of the inventive methods and systems disclosed herein.
Figure 5B:
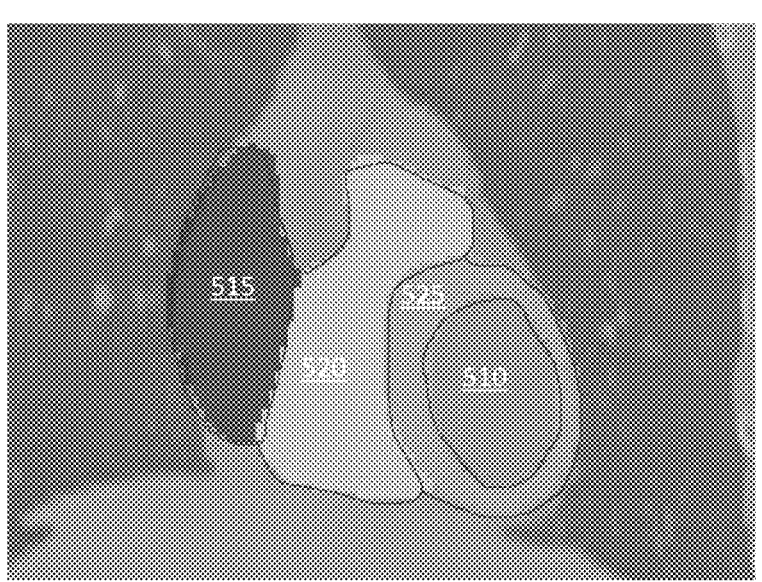
Figure 5C:
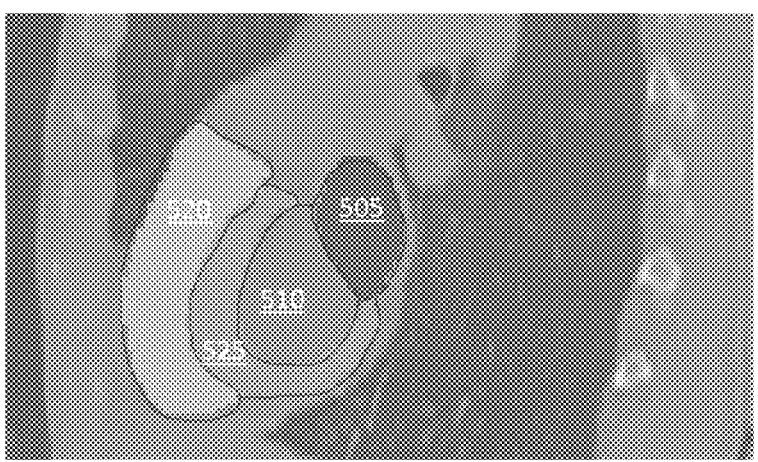

5A-5C show an example of segmentations for cardiac chambers volume measurements performed by, and according to, embodiments of the inventive methods and systems disclosed herein. Referencing FIG. 5A, in one embodiment system 200 can output to display 220 an axial view of cardiovascular structures segmented as LA 505, LV 510, RA 515, RV 520, and LV mass 525. For clarity, the various cardiovascular structures shown in FIG. 5A-5C are outlined; however, in some embodiments the cardiovascular structures can be displayed in suitable colors (such as red for LA 505, green for LV 510, blue for RA 515, yellow for RV 520, and turquoise for LV mass 525). FIG. 5A-5C are, respectively, axial, coronal, and sagittal views of cardiovascular structures.

Figure 6:
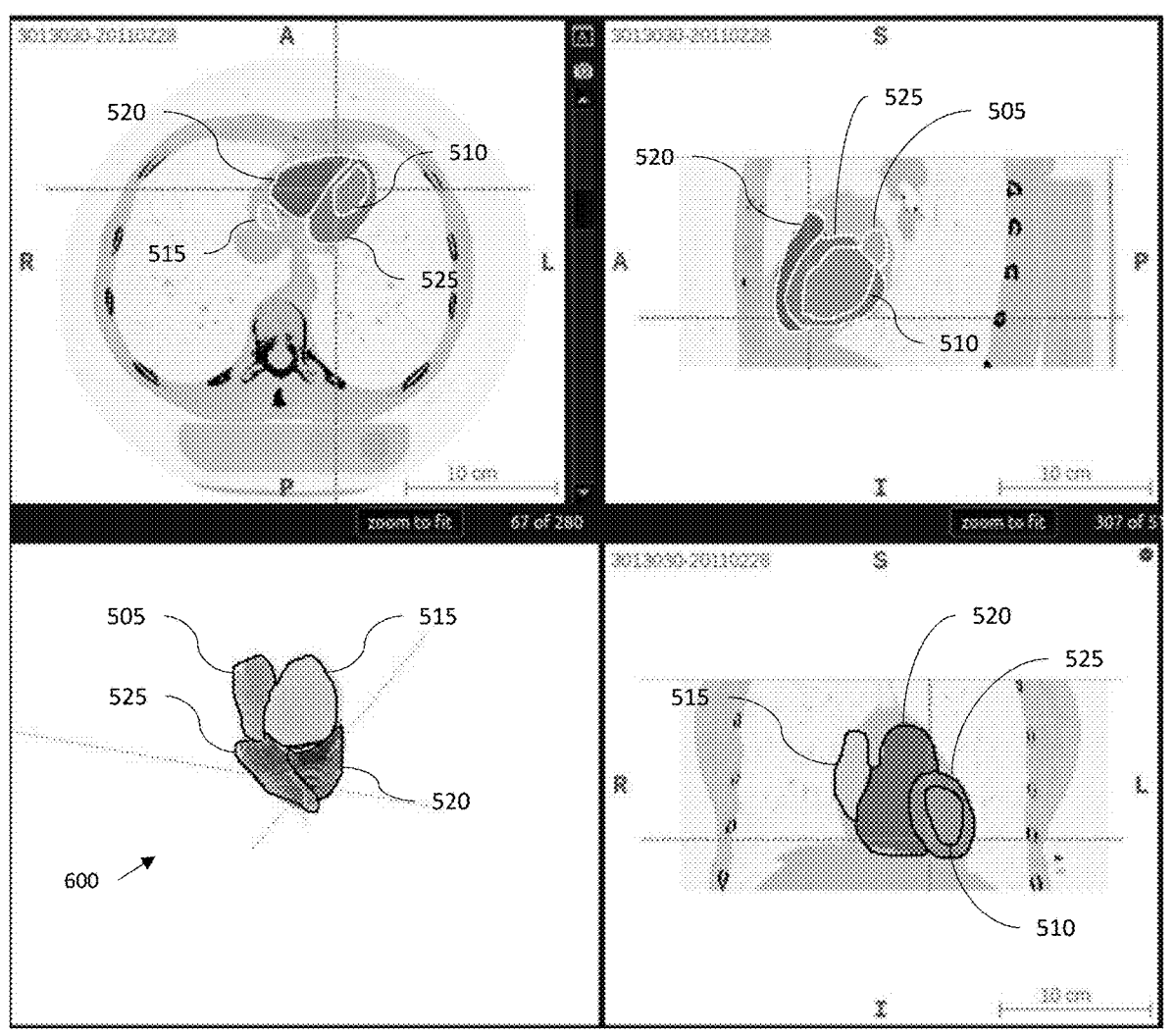
FIG. 6 shows examples of computer display images of segmentations for cardiovascular structure volume measurements performed by, and according to, embodiments of the inventive methods and systems disclosed herein.
Figures 7A, 7B:
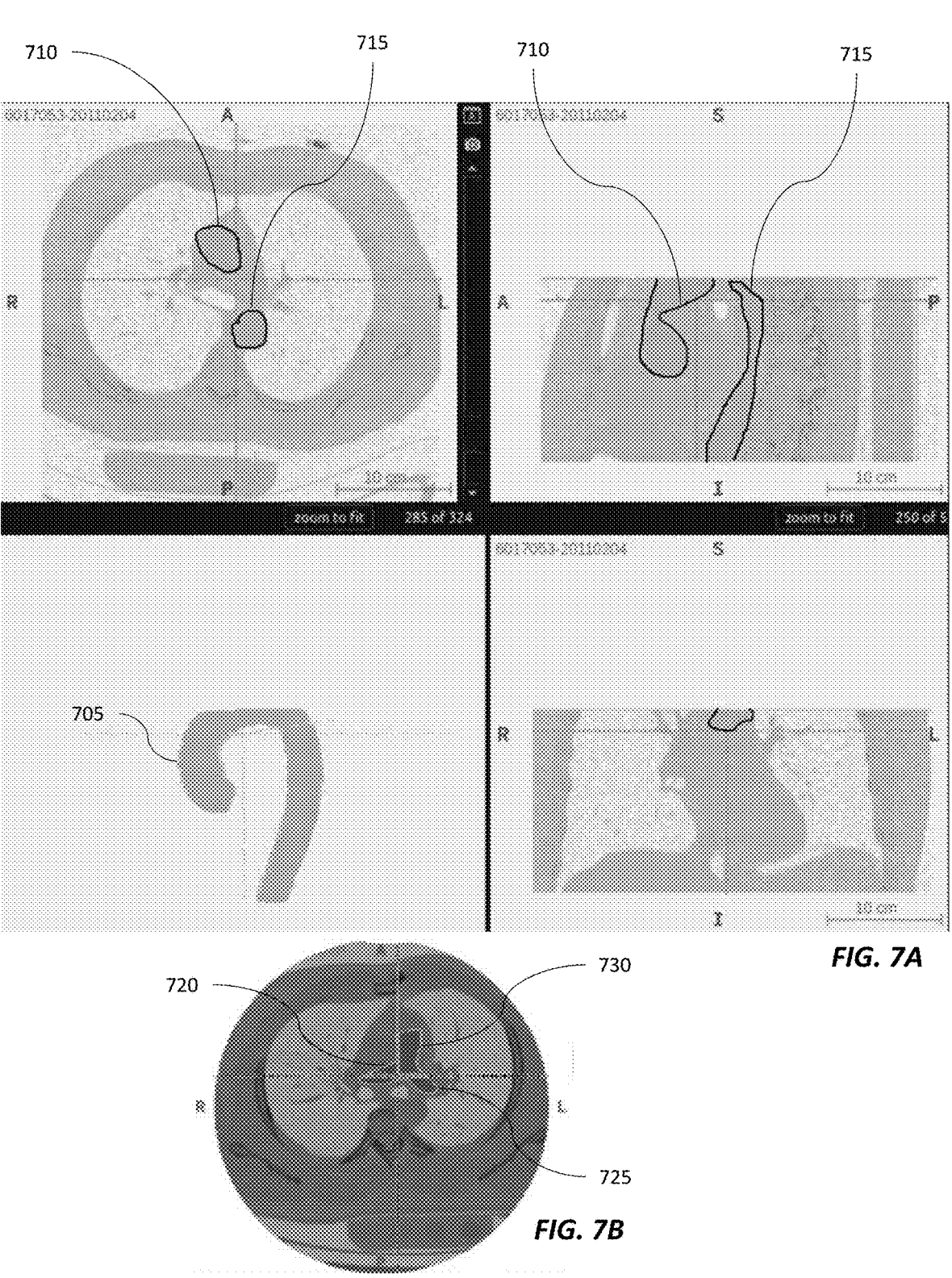
FIG. 7A and FIG. 7B show additional examples of computer display images of segmentations for cardiovascular structure volume measurements performed by, and according to, embodiments of the inventive methods and systems disclosed herein.

FIG. 6 shows examples of computer display images of segmentations for cardiovascular structure volume measurements performed by, and according to, embodiments of the inventive methods and systems disclosed herein. Image 600 shows a three-dimensional representation of the shapes and volumes of the cardiovascular structures. FIG. 7A-7B show segmentations for the aorta 705, ascending pulmonary arteries 710, descending pulmonary artery 715, right pulmonary artery 720, left pulmonary artery 725, and pulmonary trunk 730.

Figure 8A:
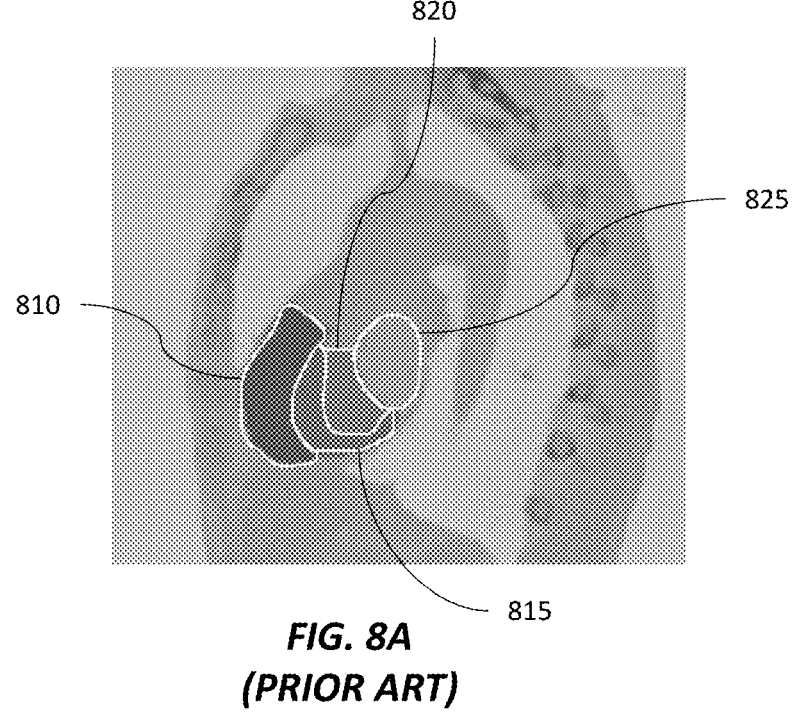
FIG. 8A shows LV segmentation and volumetry in nongated full chest CT scans performed conventionally.
Figure 8B:
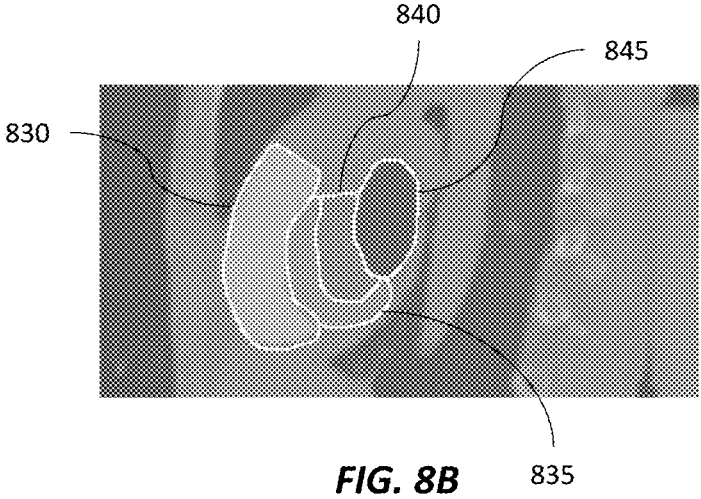
FIG. 8B shows segmentation and volumetry in ECG-gated cardiac scans performed by certain embodiments of the systems and methods disclosed herein.
Figure 10:
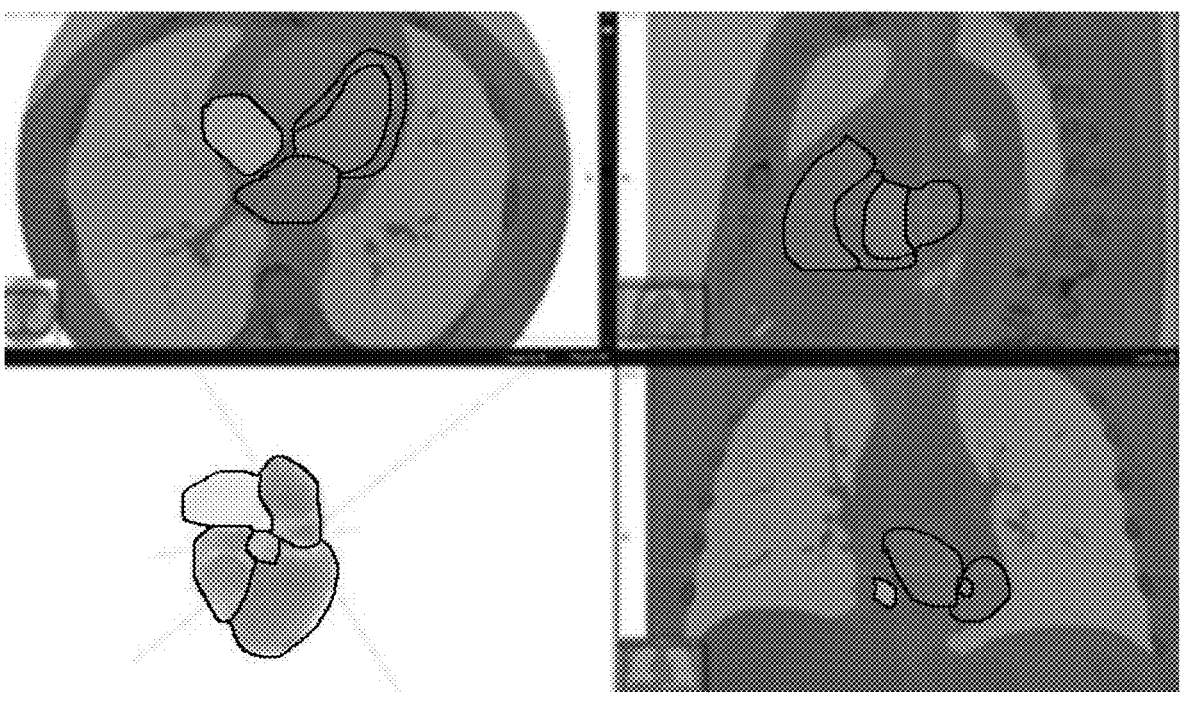
FIG. 10 shows imaging and segmentation in non-gated full chest scan for volume measurements as performed by certain embodiments of the systems and methods disclosed herein.

FIG. 8A shows LV segmentation and volumetry in non-gated full chest CT scans performed conventionally, illustrating RV 810, LV mass 815, LV 820, and LA 825. FIG. 8B shows LV segmentation and volumetry in ECG-gated cardiac scans performed by certain embodiments of the systems and methods disclosed herein, illustrating RV 830, LV mass 835, LV 840, and LA 845. FIG. 10 and FIG. 11 show segmentation performed by certain embodiments of the systems and methods disclosed herein in, respectively, non-gated full chest scans and in ECG-gated cardiac scans.

FIG. 9 is a graph illustrating a correlation associated with the LV volumetry of FIG. 8A and FIG. 8B. FIG. 12 is a graph illustrating a correlation associated with the LA volume measurements in gated cardiac CT scans versus non-gated full chest lung CT scans. FIG. 9 and FIG. 12 show that the volumes estimated by embodiments of the invention disclosed here are highly correlated with volumes estimated using conventional methods.

FIG. 13 shows cardiac structure volumetry in cardiac MRI scans performed by known methods and systems. FIG. 14 shows cardiac structure volumetry in gated cardiac CT scans performed by certain embodiments of system 200. The images shown in FIG. 13 and FIG. 14 are not associated with the same patient.

FIG. 15 is a graphic illustrating a correlation between LA maximum volume estimates performed by the inventive methods and systems disclosed here and LA maximum volume estimates performed by known methods of cardiac MRI scans. FIG. 16 is a graphic illustrating a correlation between LA minimum volume estimates performed by the inventive methods and systems disclosed here and LA minimum volume estimates performed by known methods of cardiac MRI scans.

FIG. 17 shows an exemplary image of a contrast enhanced cardiac CT angiography scan produced by conventional methods. FIG. 18 shows an exemplary image of non-contrast cardiac CT scan image segmentation performed by certain embodiments of the systems and methods disclosed herein.

FIG. 19, FIG. 20, FIG. 21, and FIG. 22 show, respectively, correlations associated with RA, RV, LA, and LV volume measurements in non-gated cardiac CT scans performed by certain embodiments of the systems and methods disclosed herein versus RA, RV, LA, LV volume measurements in gated contrast-enhanced cardiac CT scans performed by conventional methods.

FIG. 23-26 shows cumulative incidence rates of HF and AF using, respectively, LV and LA volume estimates performed by embodiments of system 200 using non-contrast CAC scans. FIG. 23 shows cumulative incidence rates of HF among certain top percentiles of LV volume estimates (N=6,398), as adjusted by age, gender, and body surface area. It is shown top 1% 2302, top 5% 2304, top 10% 2306, and top 25% 2308. FIG. 24 shows cumulative incidence rates of HF among quartiles using LV volume estimates, as adjusted by age, gender, and body surface area. It is shown first quartile 2402, second quartile 2404, third quartile 2406, and fourth quartile 2408.

FIG. 25 shows rates of AF among quartiles using LA volume estimates (N=6,334), as adjusted by age, gender, and body surface area. It is shown first quartile 2502, second quartile 2504, third quartile 2506, and fourth quartile 2508.

FIG. 26 shows cumulative incidence rates of AF among certain top percentiles using LA volume estimates, as adjusted by age, gender, and body surface area. It is shown top 1% 2602, top 5% 2604, top 10% 2606, and top 25% 2608.

Heart failure with preserved ejection fraction (HFpEF) is typically defined as heart failure with a left ventricular ejection fraction (LVEF) of 50% or greater. Heart failure with a reduced ejection fraction (HFrEF) is heart failure with an LVEF of 40% or less. FIG. 27 shows HFrEF versus HFpEF by LV volume as performed by certain embodiments of the inventive systems and methods disclosed herein. FIG. 28 shows HFrEF versus HFpEF by left ventricle volume index (LVVI) as performed by certain embodiments of the inventive systems and methods disclosed herein. LVVI is defined as LV volume divided adjusted by body surface area. Some embodiments of the inventive systems and methods disclosed herein can facilitate distinguishing whether a patient is associated with HFpEF or, rather, HFrEF. Being able to make such a distinction can facilitate selecting the most adequate healthcare intervention that applies to the patient.

FIG. 28A illustrates the prediction performance of an AI-enabled model, according to the inventive systems and methods disclosed herein, versus the prediction performance of BNP, a blood test used for heart failure studies. As shown, the AI-enabled prediction model 2850 significantly outperforms BNP prediction model 2855. The ROC Curve (Area) for AI-enable model 2850 is 0.8849 and for BNP model 2855 is 0.7660, in this example.

Referring now to FIG. 29, exemplary processing system 3100 to which the present embodiments may be applied is shown in accordance with one embodiment. System 3100 includes at least one processor (CPU) 3104 operatively coupled to other components via system bus 3102. Cache 3106, Read Only Memory (ROM) 3108, Random-Access Memory (RAM) 3110, input/output (I/O) adapter 3120, sound adapter 3130, network adapter 3140, user interface adapter 3150, and display adapter 3160, are operatively coupled to system bus 3102.

First storage device 3122 and second storage device 3124 are operatively coupled to system bus 3102 by I/O adapter 3120. Storage devices 3122 and 3124 may be any of a disk storage device (e.g., a magnetic or optical disk storage device), a solid-state magnetic device, and so forth. Storage devices 3122 and 3124 may be the same type of storage device or different types of storage devices.

Speaker 3132 is operatively coupled to system bus 3102 by sound adapter 3130. Transceiver 3142 is operatively coupled to system bus 3102 by network adapter 3140. Display device 3162 is operatively coupled to system bus 3102 by display adapter 3160.

First user input device 3152, second user input device 3154, and third user input device 3156 are operatively coupled to system bus 3102 by user interface adapter 3150. User input devices 3152, 3154, and 3156 may be any of a keyboard, a mouse, a keypad, an image capture device, a motion sensing device, a microphone, a device incorporating the functionality of at least two of the preceding devices, or any other suitable types of input devices. User input devices 3152, 3154, and 3156 may be the same type of user input device or different types of user input devices. User input devices 3152, 3154, and 3156 are used to input and output information to and from system 3100. In certain embodiments, volume calculator 205 and/or risk calculator 215 is operatively coupled to system bus 3102.

Processing system 3100 may also include other elements (not shown), as readily contemplated by one of skill in the art, as well as omit certain elements. For example, various other input devices and/or output devices may be included in processing system 3100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of system 3100 are readily contemplated by one of ordinary skill in the art given the teachings of the present disclosure provided herein.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 30, illustrative cloud computing environment 3250 is depicted. As shown, cloud computing environment 3250 includes one or more cloud computing nodes 3210 with which local computing devices used by cloud consumers, such as, for example, personal digital assistant (PDA) or cellular telephone 3254A, desktop computer 3254B, laptop computer 3254C, and/or automobile computer system 3254N may communicate. Nodes 3210 may communicate with one another. They may be grouped (not shown) physically or virtually, in one or more networks, such as Private, Community, Public, or Hybrid clouds as described hereinabove, or a combination thereof. This allows cloud computing environment 3250 to offer infrastructure, platforms and/or software as services for which a cloud consumer does not need to maintain resources on a local computing device. It is understood that the types of computing devices 3254A-N shown in FIG. 32 are intended to be illustrative only and that computing nodes 3210 and cloud computing environment 3250 can communicate with any type of computerized device over any type of network and/or network addressable connection (e.g., using a web browser).

Referring now to FIG. 31, a set of functional abstraction layers provided by cloud computing environment 3250 (FIG. 30) is shown. It should be understood in advance that the components, layers, and functions shown in FIG. 31 are intended to be illustrative only and embodiments of the invention are not limited thereto. As depicted, the following layers and corresponding functions are provided:

Hardware and software layer 3360 includes hardware and software components. Examples of hardware components include: mainframes 3361; RISC (Reduced Instruction Set Computer) architecture-based servers 3362; servers 3363; blade servers 3364; storage devices 3365; and networks and networking components 3366. In some embodiments, software components include network application server software 3367 and database software 3368.

Virtualization layer 3370 provides an abstraction layer from which the following examples of virtual entities may be provided: virtual servers 3371; virtual storage 3372; virtual networks 3373, including virtual private networks; virtual applications and operating systems 3374; and virtual clients 3375.

In one example, management layer 3380 may provide the functions described below. Resource provisioning 3381 provides dynamic procurement of computing resources and other resources that are utilized to perform tasks within the cloud computing environment. Metering and Pricing 3382 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 3383 provides access to the cloud computing environment for consumers and system administrators. Service level management 3384 provides cloud computing resource allocation and management such that required service levels are met. Service Level Agreement (SLA) planning and fulfillment 3385 provide pre-arrangement for, and procurement of, cloud computing resources for which a future requirement is anticipated in accordance with an SLA.

Workloads layer 3390 provides examples of functionality for which the cloud computing environment may be utilized. Examples of workloads and functions which may be provided from this layer include: mapping and navigation 3391; software development and lifecycle management 3392; virtual classroom education delivery 3393; data analytics processing 3394; transaction processing 3395; and neural network CECT CP classification processing 3396.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a wave-guide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions.

The descriptions of the various embodiments have been presented for purposes of illustration and are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A computer-implemented method for determining a risk of cardiovascular disease from CT scan images using an artificial intelligence (AI), the method comprising:

receiving one or more CT scan images containing a patient's heart via a user input device;

preprocessing, by at least one processor, the one or more CT scan images to improve image quality for analysis;

processing, by the least one processor, the preprocessed one or more CT scan images using a cardiovascular structure AI model to generate segmentation masks for each cardiovascular structure and distinguish blood inside the cardiovascular structure from the wall of the cardiovascular structure;

refining the segmentation masks with a post-processing module to improve accuracy;

generating, by the at least one processor, three-dimensional representation of the segmented cardiovascular structures and spatial visualization overlays of the segmented cardiovascular structures onto the original CT images using distinct color codes;

identifying and delineating with voxel level resolutions, by the at least one processor, the boundaries of the three-dimensional segmented cardiovascular structures, including the left atrium (LA), the left ventricle (LV), the right atrium (RA), the right ventricle (RV), and the left ventricular mass (LVM), and quantifying volumes of each of the identified cardiovascular structures (LA, LV, RA, RV, LVM) based on three dimensional parameters of each of the identified cardiovascular structures;

comparing, by the at least one processor, the quantified volumes to a set of reference values derived from a population database, wherein the reference values are stratified by at least one of age, gender, and body surface area;

inputting the calculated volumes and patient-specific data by at least one of age, gender, and body surface area into a cardiovascular risk prediction model trained on clinical outcomes data and cardiovascular structure volumes to predict adverse health outcomes;

computing, by the at least one processor and by using the cardiovascular risk prediction model, the risk of developing at least one adverse health condition selected from the group consisting of atrial fibrillation (AF), heart failure (HF), stroke, and cardiac mortality; and outputting, by an output medium, a report comprising a cardiovascular disease risk score adjusted by the at least one of age, gender, and body surface area.

2. The method of claim 1, wherein the one or more CT scan image is selected from the group consisting of contrast enhanced and non-contrast enhanced CT scan images, ECG-gated cardiac CT scan images, non-gated cardiac CT scan images, non-gated full chest CT scan images, low dose lung cancer screening CT scan images, and lung diagnostic CT scan images.

3. The method of claim 1 further comprises a step of combining the volume of cardiovascular structures with one or more health related variables resulting in a multivariate composite index to determine the risk of future adverse cardiovascular conditions.

4. The method of claim 1 is operating in a cloud infrastructure on a computing environment.

5. The method of claim 1 further comprises steps for training the cardiovascular structure AI model, wherein the steps include:

acquiring paired contrast-enhanced and non-contrast enhanced images of the heart chambers, aorta and pulmonary arteries including the pulmonary trunk;

manually creating labels for each cardiac chamber using contrast-enhanced image as the guide; and co-registering or aligning the labeled contrast-enhanced images over the non-contrast enhanced images and creating a unified image as the input to train a UNET neural network for measuring the volume of cardiovascular structures.

6. The method of claim 1, wherein the cardiovascular disease includes atrial fibrillation, heart failure, stroke, coronary heart disease, cerebrovascular events, chronic obstructive pulmonary diseases (COPD), emphysema, ischemic heart disease, cardiovascular mortality, and all-cause mortality.

7. A system for detecting a patient at risk of a cardiovascular disease, the system comprising:

an input medium;

at least one processor, a computer-readable medium storing computer-readable instructions; and an output medium, wherein the system receives, using the input medium, one or more non-invasive cardiac scan images of the patient's heart, wherein the one or more images are acquired from a modality selected from the group consisting of a computed tomography (CT) scan, an echocardiographic scan, and a magnetic resonance imaging (MRI) scan;

preprocesses, using the least one processor, the one or more cardiac scan images to improve image quality for analysis;

processes, using the at least one processor, the preprocessed images using a cardiovascular structure AI model to generate segmentation masks for each cardiovascular structure and distinguish blood inside the cardiovascular structure from the wall of the cardiovascular structure;

refines the segmentation with a post-processing module to improve accuracy;

generates, using the at least one processor, three-dimensional representation of the segmented cardiovascular structures and spatial visualization overlays of the segmented cardiovascular structure onto the original CT images, using distinct color codes;

identifies and delineates with voxel level resolutions using the at least one processor the boundaries of the three-dimensional segmented cardiovascular structures, including the left atrium (LA), the left ventricle (LV), the right atrium (RA), the right ventricle (RV), and the left ventricular mass (LVM), and quantify volumes of each of the identified cardiovascular structures (LA, LV, RA, RV, LVM) based on three dimensional parameters of each of the identified cardiovascular structures;

compares, using the at least one processor, the quantified volumes to a set of reference values derived from a population database, wherein the reference values are stratified by at least one of age, gender, and body surface area;

computes, using the at least one processor, the adjusted volumes based on patient-specific data including at least one of the patient's age, gender, and body surface area;

inputs the patient-specific adjusted volumes into a cardiovascular risk prediction model, the model having been trained on clinical outcome data correlating the volumes of cardiovascular structures with adverse health outcomes;

computes, using the cardiovascular risk prediction model, the risk of developing at least one adverse health condition selected from the group consisting of atrial fibrillation (AF), heart failure (HF), stroke, and cardiac mortality; and outputs, using the output medium, a report comprising the risk of developing at least one adverse health condition selected from the group consisting of atrial fibrillation (AF), heart failure (HF), stroke, and cardiac mortality.

8. A system for detecting a patient at risk of developing atrial fibrillation (AF), the system comprising:

an input medium;

at least one processor;

a computer-readable medium storing computer-readable instructions; and an output medium, wherein the system receives, using the input medium, one or more non-invasive cardiac scan images of the patient's heart, wherein the one or more images are acquired from a modality selected from the group consisting of a computed tomography (CT) scan, an echocardiographic scan, and a magnetic resonance imaging (MRI) scan;

preprocesses, using the at least one processor, the one or more noninvasive scan images to improve image quality for analysis;

processes, using the at least processor, the preprocessed images using a cardiovascular structure AI model to generate a segmentation mask of the left atrium (LA) and distinguish blood inside LA from the wall of LA;

refines the segmentation with a post-processing module to improve accuracy;

generates, using the at least one processor, a three-dimensional representation of the segmented LA and spatial visualization overlay of the segmented LA on the original images, using a distinct color code;

identifies and delineates with voxel level resolutions the boundaries of the segmented LA and quantify the volume based on three-dimensional parameters of the segmented LA;

compares, using the at least one processor, the quantified LA volume to a set of reference values derived from the population database, wherein the reference values are stratified by at least one of age, gender, and body surface area;

compute, using the at least one processor, the adjusted LA volume based on patient-specific data including at least one of the patient's age, gender, and body surface area;

inputs the patient-specific adjusted LA volume into an AF risk prediction model, the model having been trained on clinical outcome data correlating LA volume with incidence of atrial fibrillation in a population;

computes an AF risk score for the patient using the AF risk prediction model, wherein the AF risk score is determined based on the patient's adjusted LA volume and wherein a larger LA volume (a higher percentile) corresponds to a higher risk of AF; and outputs a report comprising the patient's atrial fibrillation risk score via the output medium.

9. The system of claim 8 further comprising a computer enabled health adviser configured, based on the LA volume and a patient's age, gender, ethnicity, body surface size, and other health related conditions, for recommending a cardiac monitoring device for monitoring episodes of AF and/or for alerting patients to take preventive actions against a future cerebrovascular event.

10. The system of claim 9, wherein the cardiac monitoring device is one from the group comprising: implantable ECG devices, wearable ECG devices, ECG patches, ECG embedded blood pressure cuffs, photoplethysmography (PPG) devices, and wearables devices capable of detecting AF and alerting the patient.

11. The system of claim 8, wherein the risk calculator is further configured to determine, based at least in part on one or more health related variables resulting in a multivariate composite index to estimate the risk of developing AF and stroke.

12. A system for detecting a patient at risk of developing heart failure with reduced ejection fraction (HFrEF) versus heart failure with preserved ejection fraction (HFpEF), comprising an input medium; at least one processor; a computer-readable medium storing computer-readable instructions; and an output medium, wherein the system receives, by the input medium, a plurality of non-invasive cardiac scan images of the patient's heart, wherein the images are obtained from at least one modality selected from the group consisting of a computed tomography (CT) scan, an echocardiographic scan, and a magnetic resonance imaging (MRI) scan;

preprocesses, by the at least one processor, the one or more cardiac scan images to enhance image quality for analysis;

processes, by the at least one processor, the preprocessed images using a cardiovascular structure AI model to generate segmentation masks for each cardiovascular structure and distinguish blood inside the cardiovascular structure from the wall of the cardiovascular structure;

refines the segmentation with a post-processing module to improve accuracy;

generates three-dimensional representation of the segmented cardiovascular structures and spatial visualization overlays of the segmented cardiovascular structure onto the original images, using distinct color codes;

identifies and delineates with voxel level resolutions the boundaries of the three-dimensional segmented cardiovascular structures including the left atrium (LA), the left ventricle (LV), the right atrium (RA), the right ventricle (RV), and the left ventricular wall (LVW), and quantify volumes of the segmented cardiac structures (including at least the LA, LV, RA, RV, and LVW) based on the segmentation data;

adjusts, by the at least one processor, each calculated chamber volume based on patient-specific parameters including at least the patient's age, gender, and body surface area, thereby normalizing the volumes for the patient's body size and demographics;

compares the quantified volumes to a set of reference values derived from the population database, wherein the reference values are stratified by at least one of age, gender, and body surface area;

adjusts the quantified volumes based on patient-specific data including at least one of the patient's age, gender, and body surface area (BSA);

inputs the patient-specific adjusted volumes data into a heart failure risk prediction model, the model being trained on clinical data to correlate patterns of cardiac chamber volumes with the likelihood of HFrEF or HFpEF;

computes a heart failure risk score for the patient using the heart failure risk prediction model, wherein the risk outcome indicates a likelihood of the patient developing HFrEF versus HFpEF, and wherein an abnormally elevated LV volume is indicative of a higher risk of HFrEF while a relatively normal an abnormally elevated LV mass and relatively normal LV volume (with other volume indicators, such as an enlarged LA or thickened LV wall, if present) is indicative of a higher risk of HFpEF; and outputs, by the output medium, a report identifying the patient's heart failure risk, including an indication of whether the patient is at greater risk for HFrEF or for HFpEF based on the volumetric analysis.

13. The system of claim 12 further comprises a computer enabled health adviser configured to, based at least on patient's age, gender, ethnicity, body surface area, cardio-metabolic risk factors, past medical history, and other health related conditions, facilitate recommending a treatment plan to take preventive actions against a future cardiovascular event.

* * * * *